US012648759B2

(12) United States Patent
Hashimoto

(10) Patent No.: US 12,648,759 B2
(45) Date of Patent: Jun. 9, 2026

(54) DEVICE, METHOD, AND RECORDING MEDIUM FOR CONTRAST-ENHANCED ULTRASONIC EXAMINATION

(71) Applicant: GE Precision Healthcare LLC, Waukesha, WI (US)

(72) Inventor: Hiroshi Hashimoto, Hino (JP)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/749,243

(22) Filed: Jun. 20, 2024

(65) Prior Publication Data

US 2024/0423590 A1 Dec. 26, 2024

(30) Foreign Application Priority Data

Jun. 20, 2023 (JP) ................................. 2023-101286

(51) Int. Cl.
*A61B 8/00* (2006.01)
(52) U.S. Cl.
CPC .................................... *A61B 8/481* (2013.01)
(58) Field of Classification Search
CPC ....... A61B 8/481; A61B 8/085; A61B 5/4887; A61B 8/469; A61B 8/463; G01S 7/52039
See application file for complete search history.

(56) References Cited

U.S. PATENT DOCUMENTS

| | | | | |
|---|---|---|---|---|
| 2010/0298710 A1* | 11/2010 | Averkiou | .............. | G06T 7/0012 600/458 |
| 2012/0027282 A1* | 2/2012 | Yoshikawa | .............. | A61B 8/13 382/131 |
| 2012/0237098 A1* | 9/2012 | Rognin | ................. | G06T 7/0016 382/131 |
| 2015/0196281 A1* | 7/2015 | Takagi | ..................... | A61B 8/06 600/408 |

(Continued)

FOREIGN PATENT DOCUMENTS

| | | |
|---|---|---|
| JP | 2013503655 A | 2/2013 |
| JP | 2020503136 A | 1/2020 |

(Continued)

OTHER PUBLICATIONS

JP application 2023-101286 filed Jun. 20, 2023—Office Action issued May 15, 2024; Machine Translation; 4 pages.
JP2022129859 English Abstract, Espacenet Aug. 12, 2024, 1 page.

*Primary Examiner* — Nyrobi Celestine
(74) *Attorney, Agent, or Firm* — SPQ IP LLC

(57) ABSTRACT

An ultrasonic diagnostic device configured to: select a first contrast image, a second contrast image, and a third contrast image; identify a first major/minor relationship based on the first contrast image, a second major/minor relationship based on the second contrast image, and a third major/minor relationship based on the third contrast image; and generate an image to determine whether contrast agent has been discharged from the target in the second and third time phases when all of the first, second, and third major/minor (Continued)

relationships indicate that the characteristic value of the target is greater than the characteristic value of the tissue, or that the characteristic value of the target is less than the characteristic value of the tissue, based on the change in the characteristic value of the target over time.

12 Claims, 20 Drawing Sheets

(56) References Cited

U.S. PATENT DOCUMENTS

| | | | | |
|---|---|---|---|---|
| 2015/0297172 A1* | 10/2015 | Takagi | .................... | A61B 8/085 |
| | | | | 600/443 |
| 2017/0071571 A1* | 3/2017 | Lee | ......................... | A61B 8/085 |
| 2017/0100101 A1* | 4/2017 | Ryoo | ................... | A61B 8/5207 |
| 2018/0185010 A1* | 7/2018 | Gu | ......................... | A61B 8/481 |
| 2019/0365344 A1* | 12/2019 | Gu | ......................... | A61B 8/085 |
| 2021/0000448 A1* | 1/2021 | Rychak | ................ | A61B 8/0883 |

FOREIGN PATENT DOCUMENTS

| | | | |
|---|---|---|---|
| JP | 7053910 | B1 | 4/2022 |
| JP | 2022129859 | A | 9/2022 |

* cited by examiner

8

1

DEVICE, METHOD, AND RECORDING MEDIUM FOR CONTRAST-ENHANCED ULTRASONIC EXAMINATION

CROSS-REFERENCE TO RELATED APPLICATIONS

This application claims priority to Japanese Patent Application No. 2023-101286, filed on Jun. 20, 2023, the disclosure of which is incorporated herein by reference in its entirety.

TECHNICAL FIELD

The present disclosure relates to an ultrasonic diagnostic device for selecting a contrast image of a certain time phase from a plurality of contrast images, and to a storage medium which stores instructions for selecting a contrast image of a certain time phase from a plurality of contrast images.

BACKGROUND

Contrast-enhanced ultrasonic examination creates an image (Wash-in Parametric Image) in which the difference in the time from the reference time of contrast-enhanced ultrasonography until the luminance of each point in the ultrasound image exceeds a threshold value (difference in the arrival time of the contrast agent) is expressed by color during the early phase. This technology is very important for target diagnosis because it allows the difference between the staining speed of the target (for example, tumor) and the staining speed of the surrounding tissue in the early phase to be represented in a single image. For example, typical liver tumors are stained earlier than liver parenchyma, so producing early phase images is extremely useful for the diagnosis of typical liver tumors.

On the other hand, the diagnostic criteria for the diagnosis of hepatocellular carcinoma using contrast-enhanced ultrasound (CT/MRI LI-RADS) also defines the timing of the contrast agent flowing out of the target and the decrease in target luminance value (Washout) as a guideline for the identification of hepatocellular carcinoma. For example, metastatic liver cancer is known to exhibit a decrease in luminance value as compared to the liver parenchyma about 1 minute after the administration of a contrast agent, and hepatocellular carcinoma (HCC) is known to have a decrease in luminance as compared to the liver parenchyma, 5 to 10 minutes after administration of the contracting agent. This suggests that not only the arrival time of the contrast agent, but also an image that expresses the timing luminance decrease of the target (Wash-out Parametric Image) would be useful.

In practice, however, the difference between the luminance value of the target (for example, tumor) and the luminance value of the liver parenchyma may be difficult to observe if the tumor has poor blood flow state or liver function, or if the ultrasound attenuation is large at depth. In such cases, it may not be possible to determine the timing when the luminance of the target decreases (Washout).

Therefore, it is desirable to develop an ultrasonic diagnostic device that can determine the timing when the luminance value of a target (for example, tumor) decreases (Washout), even when the difference between the luminance value of the target and that of the parenchyma is difficult to observe, for example, when the blood flow state of the tumor or liver function is poor, or when the ultrasound attenuation is large at depth.

2

SUMMARY

According to an aspect of the disclosure is an ultrasonic diagnostic device containing: one or more processors configured to: select from among a plurality of contrast images acquired from a cross-section containing a target of a subject to which a contrast agent has been administered, a first contrast image representing a state in which the target is stained in a first time phase, a second contrast image for determining whether the contrast agent has been discharged from the target in a second time phase after the first time phase, and a third contrast image for determining whether the contrast agent has been discharged from the target in a third time phase after the second time phase; identify a first major/minor relationship between a characteristic value of the target and the characteristic value of tissue being compared to the target in the first contrast image, a second major/minor relationship between the characteristic value of the target and the characteristic value of the tissue in the second contrast image, and a third major/minor relationship between the characteristic value of the target and the characteristic value of the tissue in the third contrast image; and generate an image to determine whether contrast agent has been discharged from the target in the second and third time phases when all of the first, second, and third major/minor relationships indicate that the characteristic value of the target is greater than the characteristic value of the tissue, or that the characteristic value of the target is less than the characteristic value of the tissue, based on the change in the characteristic value of the target over time.

According to another aspect, a storage medium that is one or more non-transitory, computer-readable recording medium storing one or more instructions executable by one or more processors, wherein the one or more instructions cause the one or more processors to perform: selecting from among a plurality of contrast images acquired from a cross-section containing a target of a subject to which a contrast agent has been administered, a first contrast image representing a state in which the target is stained in a first time phase, a second contrast image for determining whether the contrast agent has been discharged from the target in a second time phase after the first time phase, and a third contrast image for determining whether the contrast agent has been discharged from the target in a third time phase after the second time phase; identifying a first major/minor relationship between a characteristic value of the target and the characteristic value of tissue being compared to the target in the first contrast image, a second major/minor relationship between the characteristic value of the target and the characteristic value of the tissue in the second contrast image, and a third major/minor relationship between the characteristic value of the target and the characteristic value of the tissue in the third contrast image; and generating an image to determine whether contrast agent has been discharged from the target in the second and third time phases when all of the first, second, and third major/minor relationships indicate that the characteristic value of the target is greater than the characteristic value of the tissue, or that the characteristic value of the target is less than the characteristic value of the tissue, based on the change in the characteristic value of the target over time.

Effects of the Invention

For each time phase, the present disclosure specifies a major/minor relationship between a characteristic value of the target and a characteristic value of tissue being compared to the target, and determines whether all of the specified major/minor relationships indicate that the characteristic value of the target is greater (or less) than the characteristic value of the tissue. Therefore, even if the difference between the luminance of the target and the luminance of the tissue being compared is difficult to observe, it is possible to determine when the contrast agent is discharged from the target.

DETAILED DESCRIPTION

Embodiments will be described below; however, the disclosure is not limited to the following embodiments.

Figure 1:
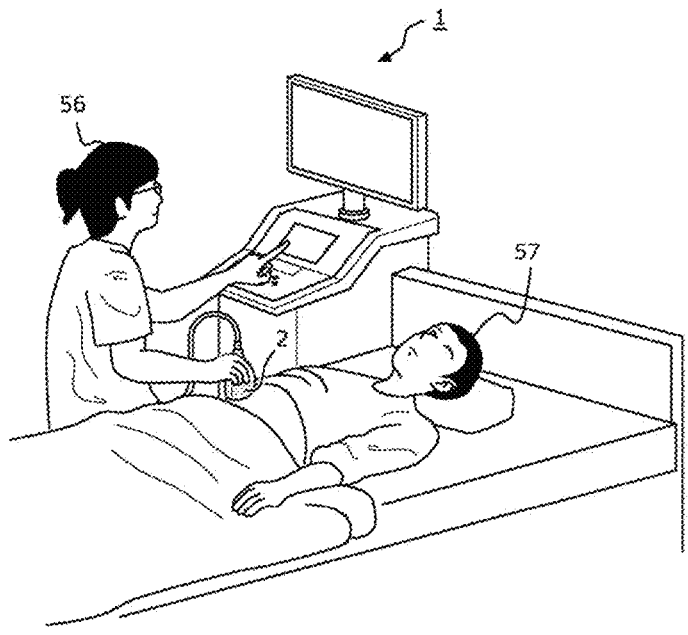
FIG. 1 is a diagram illustrating a subject being scanned using an ultrasonic diagnostic device 1 according to an embodiment.
Figure 2:
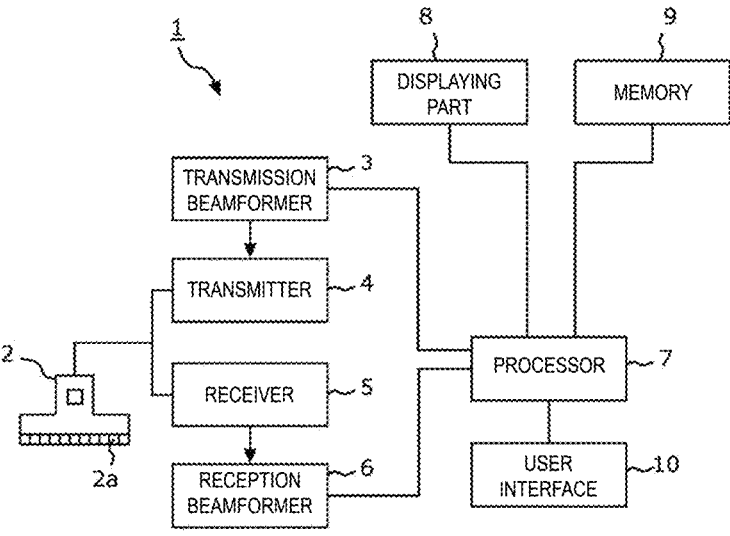
FIG. 2 is a block diagram of the ultrasonic diagnostic device 1 according to an embodiment.

FIG. 1 is a diagram illustrating a subject being scanned using an ultrasonic diagnostic device 1 according to an embodiment, while FIG. 2 is a block diagram of the ultrasonic diagnostic device 1.

The ultrasonic diagnostic device 1 has an ultrasonic probe 2, a transmission beamformer 3, a transmitting apparatus 4, a receiving apparatus 5, a reception beamformer 6, a processor 7, a display unit 8, a memory 9, and a user interface 10.

The ultrasonic probe 2 has a plurality of vibrating elements 2a arranged in an array. The transmission beamformer 3 and the transmitter 4 drive the plurality of vibrating elements 2a, which are arrayed within the ultrasonic probe 2, and ultrasonic waves are transmitted from the vibrating elements 2a. The ultrasonic waves transmitted from the vibrating element 2a are reflected in the subject 57 (see FIG. 1) and a reflection echo is received by the vibrating element 2a. The vibrating elements 2a convert the received echo to an electrical signal and output this electrical signal as an echo signal to the receiver 5. The receiver 5 executes a prescribed process on the echo signal and outputs the echo signal to the reception beamformer 6. The reception beamformer 6 executes reception beamforming on the signal received through the receiver 5 and outputs echo data.

The reception beamformer 6 may be a hardware beamformer or a software beamformer. If the reception beamformer 6 is a software beamformer, the reception beamformer 6 may include one or more processors, including one or more of: i) a graphics processing unit (GPU); ii) a microprocessor; iii) a central processing unit (CPU); iv) a digital signal processor (DSP); or v) another type of processor capable of executing logical operations. A processor configuring the reception beamformer 6 may be configured by a processor different from the processor 7 or may be configured by the processor 7.

The ultrasonic probe 2 may include an electrical circuit for performing all or a portion of transmission beamforming and/or reception beamforming. For example, all or a portion of the transmission beamformer 3, the transmitter 4, the receiver 5, and the reception beamformer 6 may be provided in the ultrasonic probe 2.

The processor 7 controls the transmission beamformer 3, the transmitter 4, the receiver 5, and the reception beam- former 6. Furthermore, the processor 7 is in electronic communication with the ultrasonic probe 2. The processor 7 controls which of the vibrating elements 2a is active and the shape of ultrasonic beams transmitted from the ultrasonic probe 2. The processor 7 is in electronic communication with the display unit 8. The processor 7 can process echo data to generate an ultrasonic image. The term "electronic communication" may be defined to include both wired and wireless communications. The processor 7 may include a central processing unit (CPU) according to one embodiment. According to other embodiment, the processor 7 may include another electronic component that may perform a processing function such as a digital signal processor, a field programmable gate array (FPGA), a graphics processing unit (GPU), another type of processor, and the like. Accord- ing to another embodiment, the processor 7 may include a plurality of electronic components capable of executing a processing function. For example, the processor 7 may include two or more electronic components selected from a list of electronic components including a central processing unit, a digital signal processor, a field programmable gate array, and a graphics processing unit.

The processor 7 may also include a complex demodulator (not illustrated in the drawings) that demodulates RF data. In another embodiment, demodulation may be executed in an earlier step in the processing chain.

Moreover, the processor 7 may generate various ultra- sonic images (for example, a B-mode image, color Doppler image, M-mode image, color M-mode image, spectral Dop- pler image, elastography image, TVI image, strain image, and strain rate image) based on data obtained by processing via the reception beamformer 6. In addition, one or a plurality of modules can generate these ultrasonic images.

An image beam and/or an image frame may be saved and timing information may be recorded indicating when the data is retrieved to the memory. The module may include, for example, a scan conversion module that performs a scan conversion operation to convert an image frame from a coordinate beam space to display space coordinates. A video processor module may also be provided for reading an image frame from the memory while a procedure is being implemented on the subject and displaying the image frame in real-time. The video processor module may save the image frame in an image memory, and the ultrasonic images may be read from the image memory and displayed on the display 8.

In the present Specification, the term "image" can broadly indicate both a visual image and data representing a visual image. Furthermore, the term "data" can include raw data, which is ultrasonic data before a scan conversion operation, and image data, which is data after the scan conversion operation.

Note that the processing tasks described above handled by the processor 7 may be executed by a plurality of processors.

Furthermore, when the reception beamformer 6 is a software beamformer, a process executed by the beam- former may be executed by a single processor or may be executed by the plurality of processors.

The display unit 8 can be an LED (light emitting diode) display, an LCD (liquid crystal display), or an organic EL (electro-luminescence) display, or the like. The display unit

8 may be configured of a single display or may include two or more displays. Furthermore, the display unit 8 may also include a touch panel.

The memory 9 is any known data storage medium. In one example, the ultrasonic diagnostic device includes a non- transitory storage medium and a transitory storage medium. In addition, the ultrasonic diagnostic device may also include a plurality of memories. The non-transitory storage medium can be, for example, a non-volatile storage medium such as a hard disk drive (HDD) drive, a read-only memory (ROM), and the like. The non-transitory storage medium may include a portable storage medium such as a CD (compact disk) or a DVD (digital versatile disk). A program executed by the processor 7 is stored in the non-transitory storage medium. The transitory storage medium is a volatile storage medium such as random-access memory (RAM).

The memory 9 stores one or more commands that can be executed by the processor 7. One or more commands cause the processor 7 to execute predetermined operations Note that the processor 7 may also be configured so as to be able to connect to an external storage device by a wired connection or a wireless connection. In this case, the com- mand causing execution by the processor 7 can be distrib- uted to both the memory 9 and the external storage device for storage.

The user interface 10 may accept input from an operator 56. For example, the user interface 10 accepts commands and information input from an operator 56. The user inter- face 10 includes a touch panel and an operating panel. The operating panel can be configured so as to include a key- board, a hard key, a trackball, a rotary controller, or the like. The touch panel can also display soft keys, buttons, and the like.

The ultrasonic diagnostic device 1 is configured as described above.

Next, the operation of the ultrasonic diagnostic device 1 in the present example will be described. In the present embodiment, an example will be described in which the ultrasonic diagnostic device 1 operates so as to acquire data of a contrast image of a subject and creates an image indicating the timing when the contrast agent is discharged from the target, based on the data of the acquired contrast image.

First, a method for acquiring data of a contrast image will be described. Specifically, the contrast image data is acquired as follows.

Figure 3:
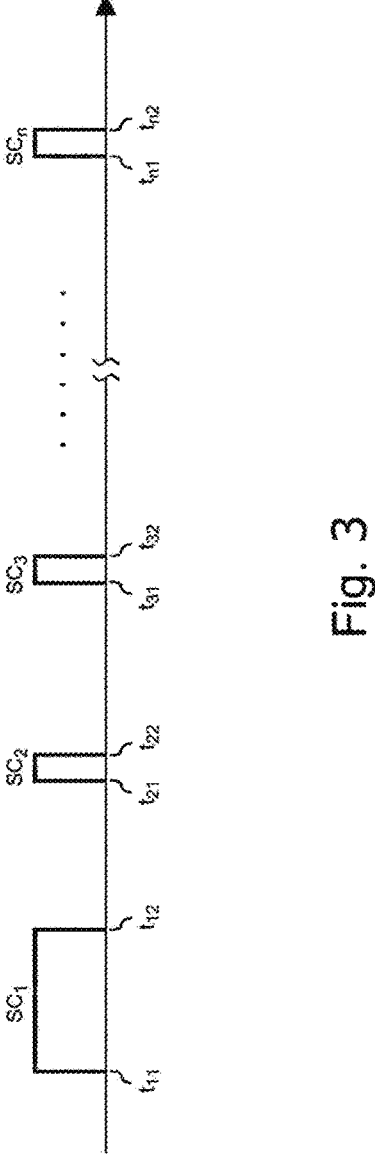
FIG. 3 is an explanatory diagram of a timeline on which a contrast image is acquired according to an embodiment.

FIG. 3 is an explanatory diagram of a time line on which a contrast image is acquired.

The operator 56 injects a contrast agent into the subject 57 and acquires a contrast image. A contrast agent containing micro-bubbles as an active ingredient can be used as the contrast agent. The operator 56 operates a probe 2 to start acquisition of a contrast image at the examination site from time point t11 (a time point at which the contrast agent is injected or a time point close to the time point at which the contrast agent is injected).

The processor 7 controls the ultrasonic probe 2 to transmit ultrasonic waves to the subject 57. The ultrasonic probe 2 receives ultrasonic waves (an echo) reflected by the contrast agent. The processor 7 performs predetermined processing on the echo signals and creates data indicating the signal intensity of the ultrasonic waves reflected by the contrast agent. Data indicating the signal intensity of the ultrasonic waves reflected by the contrast agent can be obtained as contrast image data.

The operator 56 acquires contrast image data intermit- tently over a predetermined time period from time point t11.

For example, the operator 56 acquires contrast images intermittently over a period from time t11 to time tn2. The length of time from time point t11 to time point tn2 can be set to, for example, approximately 15 minutes.

During the period from time t11 to time tn2, the operator 56 does not continuously perform ultrasonic scanning and image recording, but rather performs data collection at the predetermined times. In the present embodiment, data acquisition of the subject 57 is performed continuously during the period SC1 (time point t11 to t12), followed by data acquisitions SC2 to SCn which are performed for a few seconds each time a certain period of time elapses. In the present embodiment, the subject 57 is scanned in accordance with the time line illustrated in FIG. 3.

Figure 4:
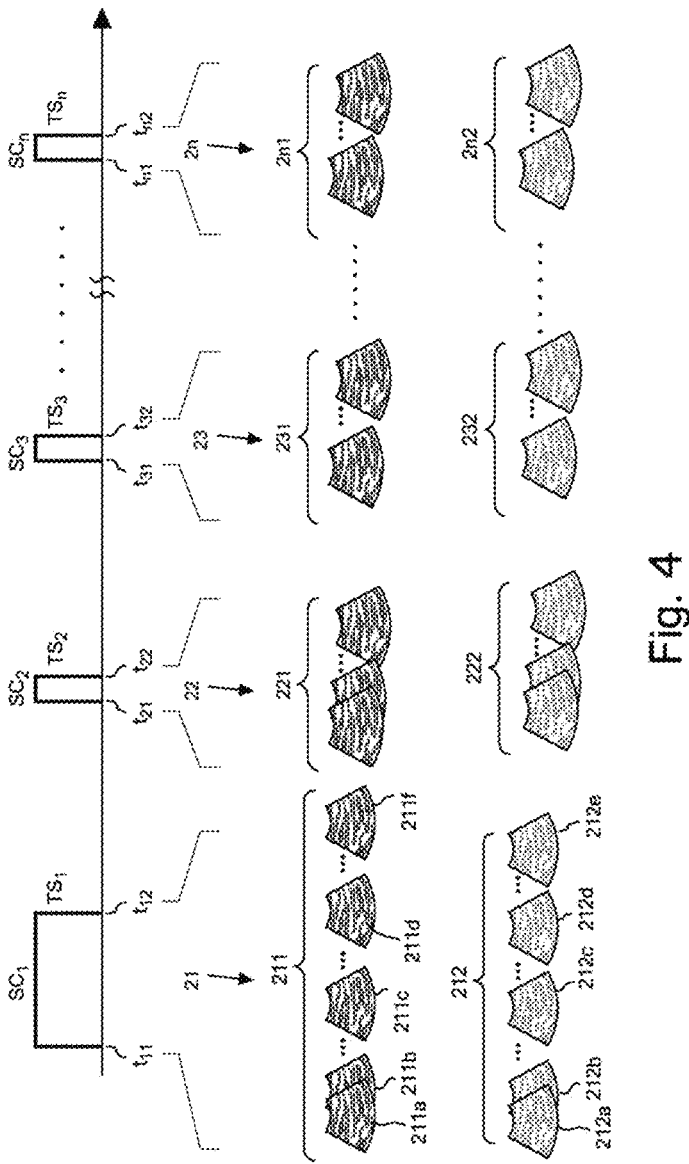
FIG. 4 is an explanatory diagram of data acquired according to the timeline illustrated in FIG. 3 according to an embodiment.

FIG. 4 is an explanatory diagram of data acquired according to the time line illustrated in FIG. 3.

First, the operator 56 administers a contrast agent, continuously performs scanning during period SC1 (between time points t11 and t12), and acquires data of an image group 21 including a plurality of ultrasonic images. The length of time from time t11 to t12 is represented by "TS1". In the present embodiment, the length of time TS1 is 60 seconds, but the length of time TS1 may be shorter or longer than 60 seconds. Between time points t11 and t12, the processor 7 controls the ultrasonic probe 2 to transmit ultrasonic waves to the subject 57. The ultrasonic probe 2 receives ultrasonic waves (an echo) reflected by the contrast agent. The processor 7 performs predetermined processing on the echo signals and creates an ultrasonic image indicating the signal intensity of the ultrasonic waves reflected by the contrast agent. The ultrasonic image can be, for example, a cross-sectional image of the liver of the subject 57. The processor 7 stores the acquired data of the image group 21 in the memory 9. In the present embodiment, two types of ultrasonic images are created as ultrasound images. One is a contrast image in which nonlinear signals included in echo signals reflected by the contrast agent are enhanced, while the other is a B-mode image. Therefore, the image group 21 contains a contrast image set 211 including a plurality of contrast images arranged in a time series and a B mode image set 212 including a plurality of B-mode images arranged in a time series.

After acquiring data from time points t11 to t12, the operator 56 interrupts the data acquisition and stands by until time point t21 at which the next data acquisition is started following injection of the contrast agent. Furthermore, the operator 56 acquires data during time period SC2 (between time point t21 and t22). Time length of period SC2 can be, for example, 5 seconds. The processor 7 performs predetermined processing on the echo signals to create image group 22. The image group 22 contains a contrast image set 221 including a plurality of contrast images arranged in a time series and a B mode image set 222 including a plurality of B-mode images arranged in a time series. The data for image group 22 is stored in the memory 9.

After acquiring data from time points t21 to t22, the operator 56 interrupts the data acquisition and stands by until time point t31 at which the next data acquisition is started following injection of the contrast agent. Furthermore, the operator 56 acquires data between time points t31 and t32 (time length TS3). Time length TS3 can be, for example, 5 seconds. The processor 7 performs predetermined processing on the echo signals to create image group 23. The image group 23 contains a contrast image set 231 including a plurality of contrast images arranged in a time series and a B mode image set 232 including a plurality of B-mode images arranged in a time series. The data for image group 23 is stored in the memory 9.

Subsequently, the step of acquiring data after standing by for a certain period of time is repeatedly executed.

Finally, the operator 56 acquires information during a period from time tn1 to time tn2 (time length TSn). The processor 7 performs predetermined processing on the echo signals to create image group 2n. The image group 2n contains a contrast image set 2n1 including a plurality of contrast images arranged in a time series and a B mode image set 2n2 including a plurality of B-mode images arranged in a time series. The data for image group 2n is stored in the memory 9.

Examination data on the subject 57 is acquired in this manner.

Data obtained by scanning the subject 57 is stored in the memory 9.

Next, the operator 56 creates images (hereinafter referred to as "WO images") to determine if the contrast agent has been discharged (washout) from the target in the early and late phases, based on the data acquired from the subject 57. This method of creating a WO image will now be described with reference to the flowchart in FIG. 5.

In step ST1, the contrast image of the time phase required to create the WO image is selected from among the plurality of contrast images acquired during examination of the subject. In this embodiment, the following three time phases are considered as necessary for the creation of WO images.

(1) Time phase representing the state in which the target (for example, a tumor) is stained by the contrast agent (hereinafter referred to as "staining time phase")

(2) Early phase, and (3) Late phase

The user selects the contrast image of the staining time phase, the contrast image of the early phase, and the contrast image of the late phase, and calculates the mean luminance of the target and the average luminance of the liver parenchyma for each time phase based on the selected contrast image.

The following describes how the contrast images of the staining time phase, the early phase contrast image, and the late phase contrast image, are selected, as well as how the average luminance of the target and the liver parenchyma are calculated.

First, the user is presented with an initial screen for selecting a contrast image.

Figure 6:
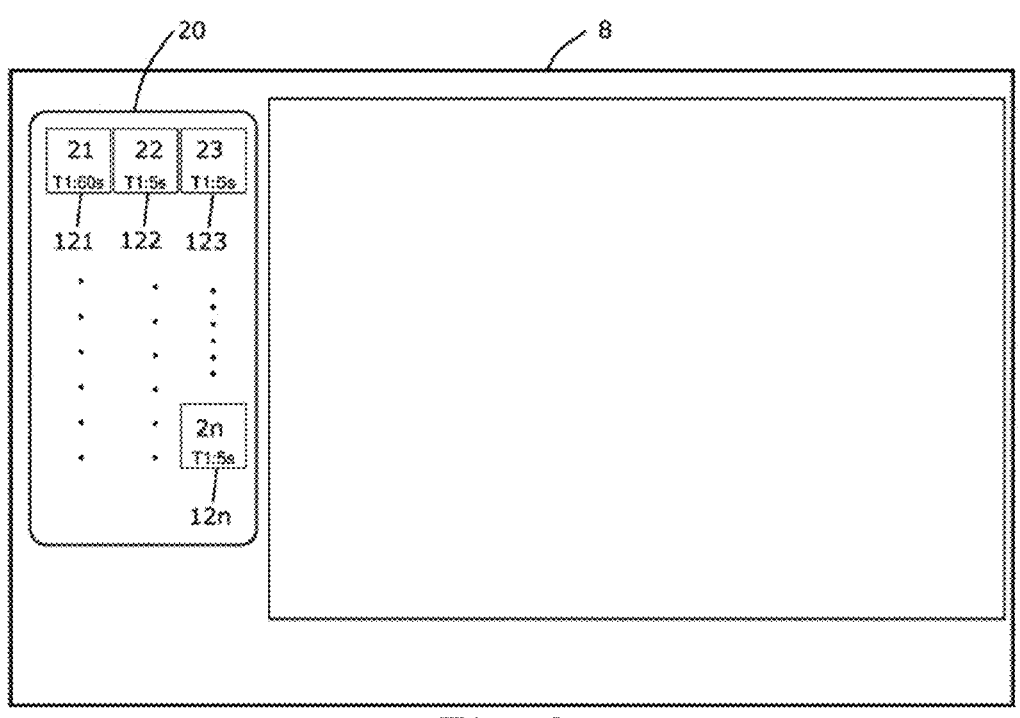
FIG. 6 is an explanatory diagram of the initial screen for selecting a contrast image according to an embodiment.

FIG. 6 is an explanatory diagram of the initial screen for selecting a contrast image.

A thumbnail region 20 is depicted on the screen of the display unit 8. The thumbnail region 20 presents n thumbnails 121 to 12n. n number of thumbnails 121 to 12n corresponding to n number of image groups 21 to 2n acquired by scanning the subject 57 are displayed. In FIG. 6, thumbnails 121, 122, 123, and 12n of four image groups 21, 22, 23, and 2n are depicted, from image groups 21 to 2n.

Herein, the method to select the contrast image of the staining time phase, the contrast image of the early phase, and the contrast image of the late phase is described.

The staining time phase is the time phase in which the target (for example, a tumor) is stained by the contrast agent, and is the time phase that appears between the time the contrast agent is administered and the time after about 1 minute has passed. On the other hand, with the present embodiment, of the image groups 21 to 2n acquired by examination of the subject, the first image group 21 represents images acquired until about 1 minute has passed after the contrast agent was administered. Therefore, the contrast image of the staining time phase is considered to be included in image group 21. Next, the user then selects an image group 21 from the thumbnail region 20.

Figure 7:
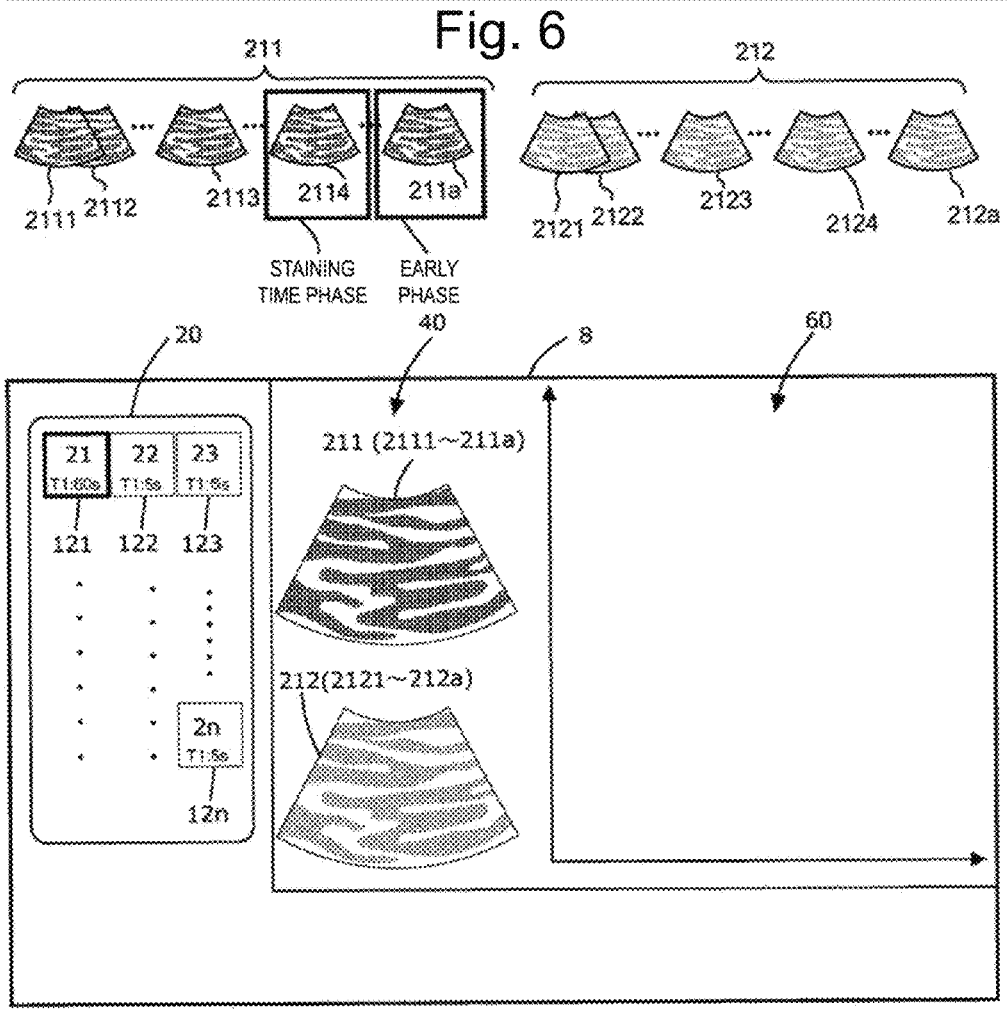
FIG. 7 is a diagram depicting the display unit after an image group 21 has been selected according to an embodiment.

FIG. 7 is a diagram depicting the display unit after an image group 21 has been selected.

The user operates the user interface 10 to input a command to select the image group 21. When the user interface 10 accepts user input to select an image group 21, the processor selects the image group 21. Note that in FIG. 7, a schematic diagram of the images included in image group 21 is depicted on the display unit 8 for reference. Image group 21 includes contrast image set 211 and B-mode image set 212. The contrast image set 211 contains contrast images 2111 to 211a, and B-mode image set 212 contains B-mode images 2121 to 212a.

When the user selects image group 21, an image from the selected image group 21 is played back in the image display region 40. In the upper half of the image display region 40, contrast images 2111 to 211a of the contrast image set 211 are reproduced, and B-mode images 2121 to 212a of the B-mode image set 212 are reproduced in the lower half. Therefore, the user can confirm images acquired between time points t11 and t12 (see FIG. 4) as video.

The user, referring to the video of contrast image set 211 (and B-mode image set 212), selects a contrast image from contrast images 2111 to 211a in contrast image set 211 from the time phase when the target (for example, a tumor) is sufficiently stained with the contrast agent. For example, if the user determines that contrast image 2114 is appropriate as a contrast image for the time phase when the target (for example, a tumor) is sufficiently stained with contrast agent from among the contrast images 2111 to 211a, the user inputs an instruction to select the contrast image 2114 from the contrast images 2111 to 211a by operating the user interface 10. When the user interface 10 accepts the user input to select the contrast image 2114, the processor selects the contrast image 2114 as the image of the staining time phase.

After selecting the contrast image 2114 of the staining time phase, the user selects the contrast image of the early phase. The early phase contrast image is the contrast image selected to determine if the contrast agent has been discharged from the target in the early phase. The early phase is the time phase when, for example, about 1 minute has passed since the contrast agent was administered. Since the contrast images 2111 to 211a are images acquired between the time the contrast agent is administered and after about 1 minute has passed, the user can find contrast images 2111 to 211a in the early phase. For example, if the user decides that contrast image 211a is appropriate as an early phase contrast image among contrast images 2111 to 211a, the user operates the user interface 10 and inputs an instruction to select contrast image 211a as an early phase contrast image. When the user interface 10 accepts user input to select contrast image 211a as the early phase contrast image, the processor selects contrast image 211a as the early phase contrast image.

In this manner, the user can select the contrast image 2114 of the staining time phase and the contrast image 211a of the early phase from the image group 21.

Figure 8:
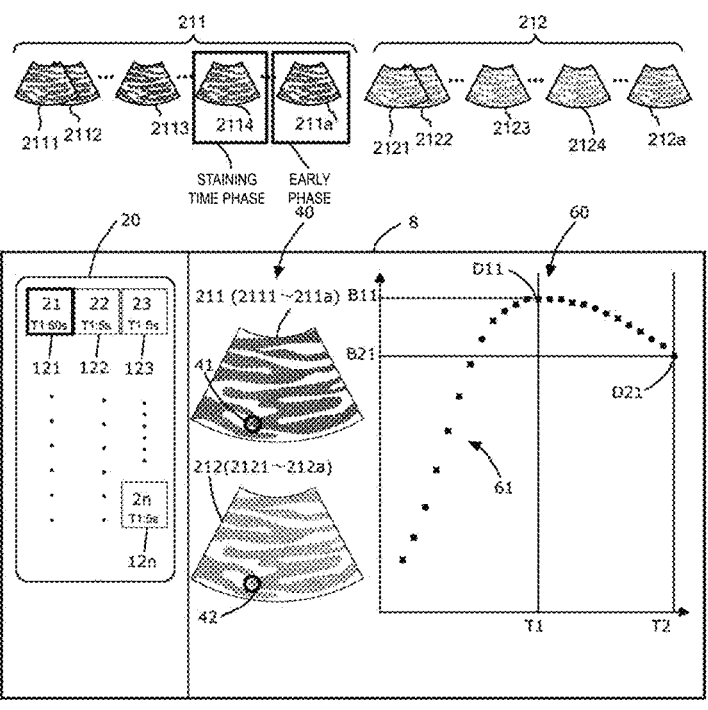
FIG. 8 is an explanatory diagram of a method of assigning a region of interest according to an embodiment.

Next, the user operates the user interface 10 to assign a region of interest on the contrast images 2111 to 211a. FIG. 8 is an explanatory diagram of a method for assigning a region of interest.

The user assigns a region of interest to a target (for example, tumor, lesion) at an inspection site while referring to the image set 211 (and 212) displayed on the image display region 40. Specifically, the user identifies the location of the target with reference to image sets 211 and 212, and enters an instruction to assign a region of interest to a target location in image sets 211 and 212. When the user interface 10 receives input from the user to assign a region of interest, the processor 7 displays a graphic figure representing regions of interest 41 and 42 on the image sets 211 and 212. In FIG. 8, the regions of interest 41 and 42 are represented by circles. The position of the region of interest 42 in the image set 212 (B-mode image) corresponds to the position of the region of interest 41 in the image set 211 (contrast image). The user can simultaneously move the regions of interest 41 and 42 by operating the user interface 10.

Once a region of interest 41 has been assigned, the processor 7 calculates a characteristic value in the region of interest 41 with respect to the contrast image 2111 to 211a of the image set 211. The characteristic value in the region of interest 41 can be calculated as, for example, a value representing luminance information in the region of interest 41. In one example, the characteristic value in the region of interest 41 can be calculated as an average value of the luminance (average luminance) or a standard deviation of the plurality of pixels included in the region of interest 41. In the following, for the sake of description, the characteristic value of the region of interest is assumed to be the average luminance. In this manner, a characteristic value in the region of interest 41 can be calculated for each contrast image 2111 to 211a in the image set 211.

Once the characteristic value of the region of interest (average luminance) is calculated, the processor displays in the TIC region 60 a group of data 61 representing the time variation of the mean luminance of the region of interest 41 calculated for the contrast images 2111 to 211a. The horizontal axis of the data set 61 represents time, while the vertical axis represents the average luminance in the region of interest. In FIG. 8, each data point included in the data set 61 is indicated by a black square. Note that in FIG. 8, the total number of data included in the data group 61 is shown as less than the actual total number of data in order to make the data group 61 easier to grasp visually. Each of the data in the data group 61 represents the average luminance of the region of interest 41 in the contrast images 2111 to 211a of image set 211. For example, data D11 represents the average luminance B11 of the target in the region of interest 41 in contrast image 2114 of the staining time phase T1, and data D21 represents the average luminance B21 of the target in the region of interest 41 in contrast image 211a of the early phase T2.

Figure 9:
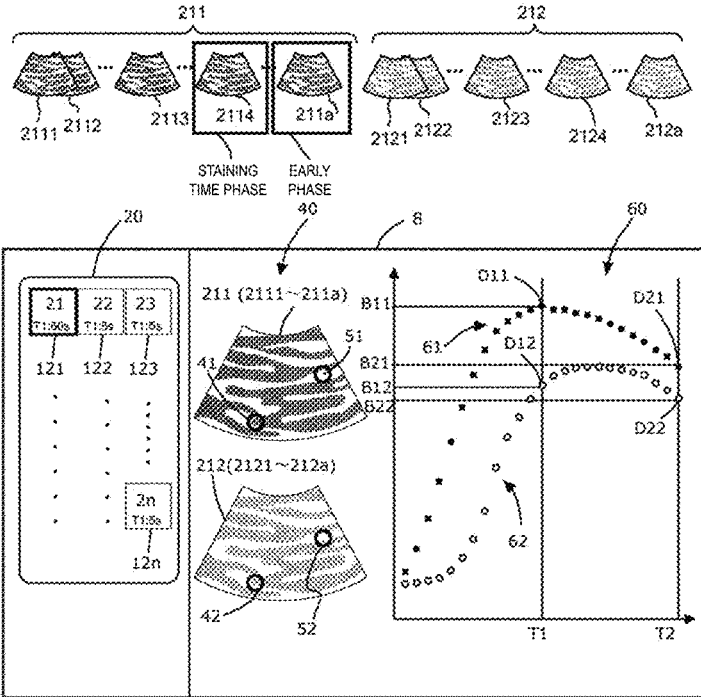
FIG. 9 is a diagram depicting a state of assigning regions of interest 51 and 52 to tissue to be compared with a target according to an embodiment.

Furthermore, the user also assigns a region of interest to the target tissue to be compared. FIG. 9 is a diagram depicting a state of assigning regions of interest 51 and 52 to tissue to be compared with a target. In this embodiment, the tissue to which the target is compared is the liver parenchyma, and an example is considered in which the region of interest 51 (and 52) is assigned to the liver parenchyma, but it is also possible to assign a region of interest to a different tissue than the liver parenchyma. After the regions of interest 51 and 52 have been assigned, the average luminance in the region of interest 51 is calculated and data group 62 representing the temporal change in the average luminance in the region of interest 51 is displayed. In FIG. 9, the data group 62 for the target comparison tissue (liver parenchyma) is indicated by a white circle. Each of the data in the data group 62 represents the average luminance of the region of interest 51 in the contrast images 2111 to 211a of image set 211. For example, data D12 represents the average luminance B12 of the liver parenchyma in the region of interest 51 in contrast image 2114 of the staining time phase T1, and data D22 represents the average luminance B22 of the liver parenchyma in the region of interest 51 in contrast image 211a of the early phase T2.

Data D11 and D12 for the staining time phase T1 and data D21 and D22 for the early phase T2 can be obtained as described above.

Finally, the user selects a late phase contrast image.

Figure 10:
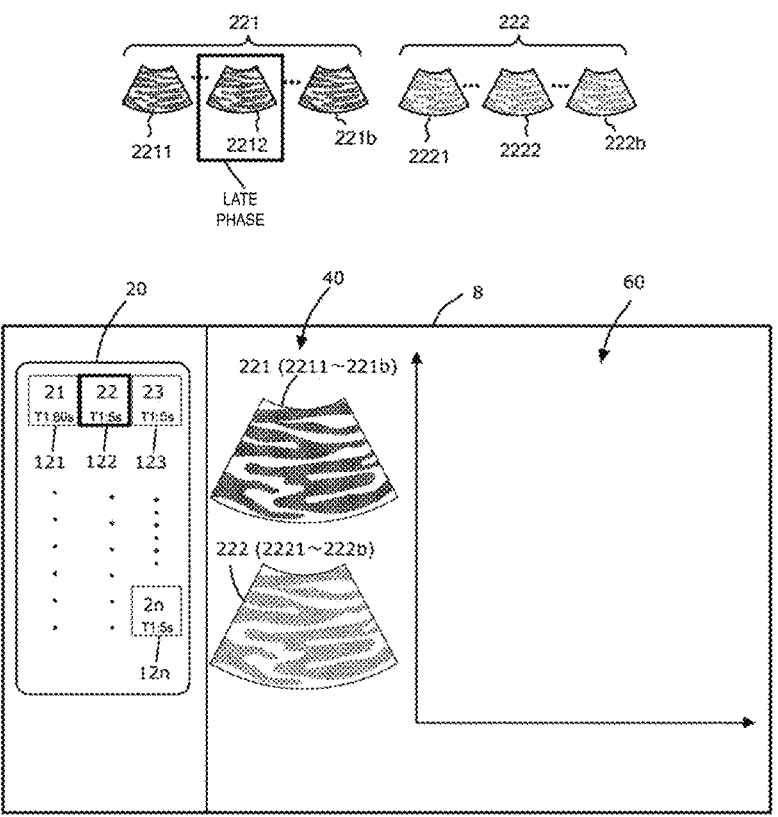
FIG. 10 is an explanatory diagram of the method of selecting a contrast image in the late phase according to an embodiment.

FIG. 10 is an explanatory diagram of the method of selecting a contrast image in the late phase.

The late phase contrast image is the contrast image selected to determine if the contrast agent has been discharged from the target in the late phase. Contrast images in the late phase generally appear between 5 and 10 minutes after the contrast agent is administered. Therefore, the user selects image groups 21 to 2n that were collected 5 to 10 minutes after the contrast agent was administered. It can be assumed that the user selects the image group 22 collected 5 minutes after the contrast agent was administered. Thus, the user operates the user interface 10 to input a command to select image group 22 that includes contrast images of the late phase from among image groups 21 to 2n. When the user interface 10 accepts the user input to select image group 22 from among a plurality of image groups 21 to 2n, the processor selects the image group 22. Note that in FIG. 10, a schematic diagram of the images included in image group 22 is depicted on the display unit 8 for reference. Image group 22 includes contrast image set 221 and B-mode image set 222. The contrast image set 221 contains contrast images 2211 to 221b, and B-mode image set 222 contains B-mode images 2221 to 222b.

When the user selects image group 22, an image from the selected image group 22 is played back in the image display region 40. In the upper half of the image display region 40, contrast images 2211 to 221b of the contrast image set 221 are reproduced, and B-mode images 2221 to 222b of the B-mode image set 222 are reproduced in the lower half. Therefore, the user can confirm images acquired between time points t21 and t22 (see FIG. 4) as video.

The user selects a late phase contrast image from the contrast images 2211 to 221b in the contrast image set 221 while referring to a video of the contrast image set 221 (and the B-mode image set 222). For example, if the user determines that contrast image 2212 is appropriate as a late phase contrast image from among contrast images 2211 to 221b, the user operates user interface 10 and inputs an instruction to select contrast image 2212 from among contrast images 2211 to 221b. When the user interface 10 accepts the user input to select the contrast image 2212, the processor selects the contrast image 2212 as the contrast image of the late phase.

Figure 11:
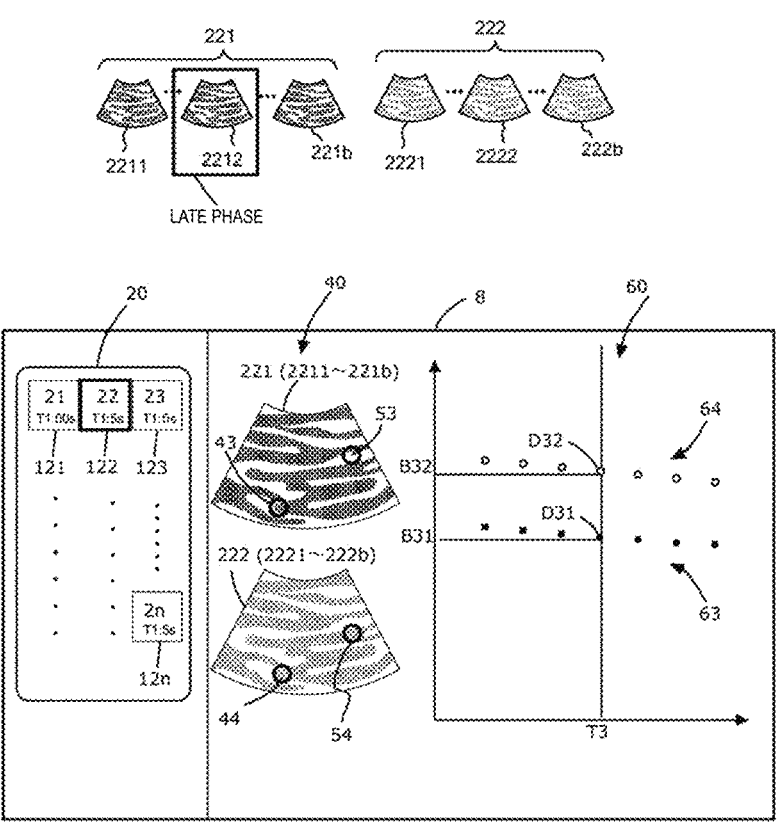
FIG. 11 is an explanatory diagram of a method of assigning a region of interest according to an embodiment.

Next, the user operates the user interface 10 to assign a region of interest on the contrast images 2211 to 221b. FIG. 11 is an explanatory diagram of a method for assigning a region of interest.

The user assigns a region of interest to a target (for example, tumor, lesion) at an inspection site while referring to the image set 221 (and 222) displayed on the image display region 40. Specifically, the user identifies the location of the target with reference to image sets 221 and 222, and enters an instruction to assign a region of interest to a target location in image sets 221 and 222. When the user interface 10 receives input from the user to assign a region of interest, the processor 7 displays a graphic figure representing regions of interest 43 and 44 on the image sets 221 and 222. In FIG. 11, the regions of interest 43 and 44 are represented by circles. The position of the region of interest 44 in the image set 222 (B-mode image) corresponds to the position of the region of interest 43 in the image set 221 (contrast image). The user can simultaneously move the regions of interest 43 and 44 by operating the user interface 10.

Once a region of interest 43 has been assigned, the processor 7 calculates a characteristic value in the region of interest 43 with respect to the contrast image 2211 to 221b of the image set 221. The characteristic value in the region of interest 43 can be calculated as, for example, a value representing luminance information in the region of interest 43. It can be assumed that the characteristic value in the region of interest 43 is the average value of the luminance of the plurality of pixels in the region of interest 43 (average luminance). Therefore, the average luminance in the region of interest 43 can be calculated for each contrast image 2211 to 221b in the image set 221.

Once the average luminance in the region of interest 43 has been calculated, the processor displays the average luminance in the region of interest 43 calculated for each contrast image 2211 to 221b in the image set 221 as depicted in the TIC region 60 of FIG. 11. The TIC region 60 depicts a data group 63 representing the time variation of the average luminance of the region of interest 43 calculated for contrast images 2211 to 221b. In FIG. 11, each data point included in the data set 63 is indicated by a black square. Note that in FIG. 11, the total number of data included in the data group 63 is shown as less than the actual total number of data in order to make the data group 63 easier to grasp visually. Each of the data in the data group 63 represents the characteristic value of the region of interest 43 in the contrast images 2211 to 221b of image set 221. For example, data D31 represents the average luminance B31 of the target in the region of interest 43 in contrast image 2212 of the late phase T3.

Furthermore, the user also assigns a region of interest to the target tissue to be compared. FIG. 11 is a diagram depicting a state of assigning regions of interest 53 and 54 to tissue to be compared with a target. In this embodiment, the tissue to be compared for the target is the liver parenchyma, and an example in which the region of interest 53 (and 54) is assigned to the liver parenchyma is considered. After the regions of interest 53 and 54 have been assigned, the average luminance in the region of interest 53 is calculated and data group 64 representing the temporal change in the characteristic value in the region of interest 53 is displayed. In FIG. 11, the data group 64 for the target comparison tissue (liver parenchyma) is indicated by a white circle. Each of the data in the data group 64 represents the characteristic value of the region of interest 53 in the contrast images 2211 to 221d of image set 221. For example, data D32 represents the average luminance B32 of the liver parenchyma in the region of interest 53 in contrast image 2212 of the late phase T3.

The data D31 and D32 for the late phase T3 can be obtained as described above.

Thus, it is possible to obtain the luminance information for the three time phases (staining time phase, early phase, and late phase) necessary to create a WO image.

Figure 12:
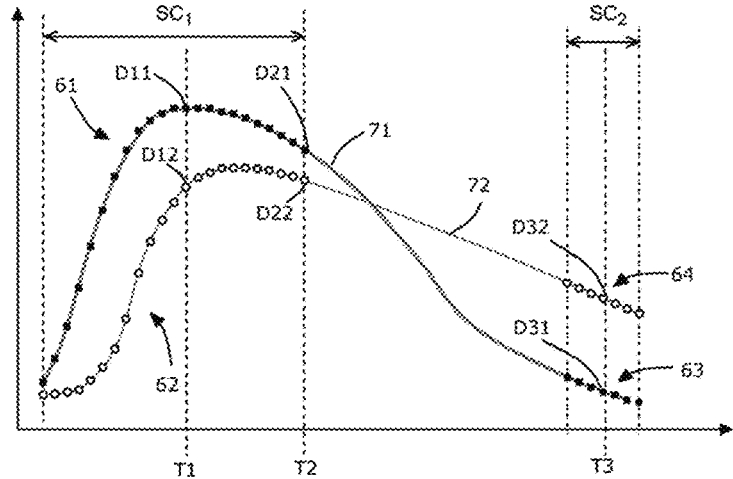
FIG. 12 is a diagram depicting comparison of data groups 61 and 62 depicted in FIG. 9 and data groups 63 and 64 depicted in FIG. 11 in chronological order according to an embodiment.

FIG. 12 is a diagram depicting comparison of data groups 61 and 62 depicted in FIG. 9 and data groups 63 and 64 depicted in FIG. 11 in chronological order.

Data groups 61 and 62 represent data groups acquired during the data acquisition period SC1 (see FIG. 4), and data groups 63 and 64 represent data groups acquired during the data acquisition period SC2 (see FIG. 4). During the data acquisition periods SC1 and SC2, no data is acquired, so no data group exists.

In addition to data groups 61 to 64, FIG. 12 depicts time-intensity curves 71 and 72. The time-intensity curve 71 is obtained by connecting the target data group 61 and data group 63 in the direction of the time axis, and the time-intensity curve 72 is obtained by connecting the liver parenchyma data group 62 and data group 64 in the direction of the time axis.

From FIG. 12, the difference can be recognized between the average luminance of the target and the average luminance of the liver parenchyma for the staining time phases T1, early phase T2, and late phase T3.

Figure 5:
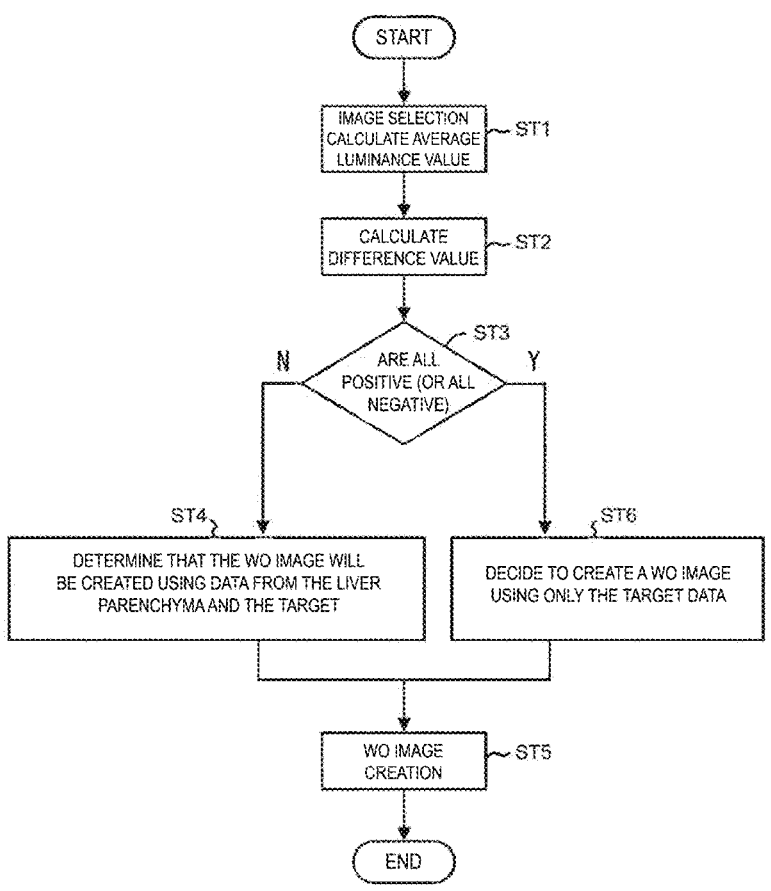
FIG. 5 is a diagram depicting a flowchart according to an embodiment.

Once the average luminance of the target and liver parenchyma in the staining time phases T1, early phase T2, and late phase T3 have been determined, the process proceeds to step ST2 (see FIG. 5).

In step ST2, the processor identifies the major/minor relationship between the average luminance of the target and the average luminance of the liver parenchyma for each of the staining time phases T1, early phase T2, and late phase T3. In the present embodiment, the case in which the difference value between the average luminance of the target and the average luminance of the liver parenchyma is calculated to identify the major/minor relationship between the average luminance of the target and the average luminance of the liver parenchyma is described, but a value other than the difference value may be calculated if it is possible to identify the major/minor relationship.

Figure 13:
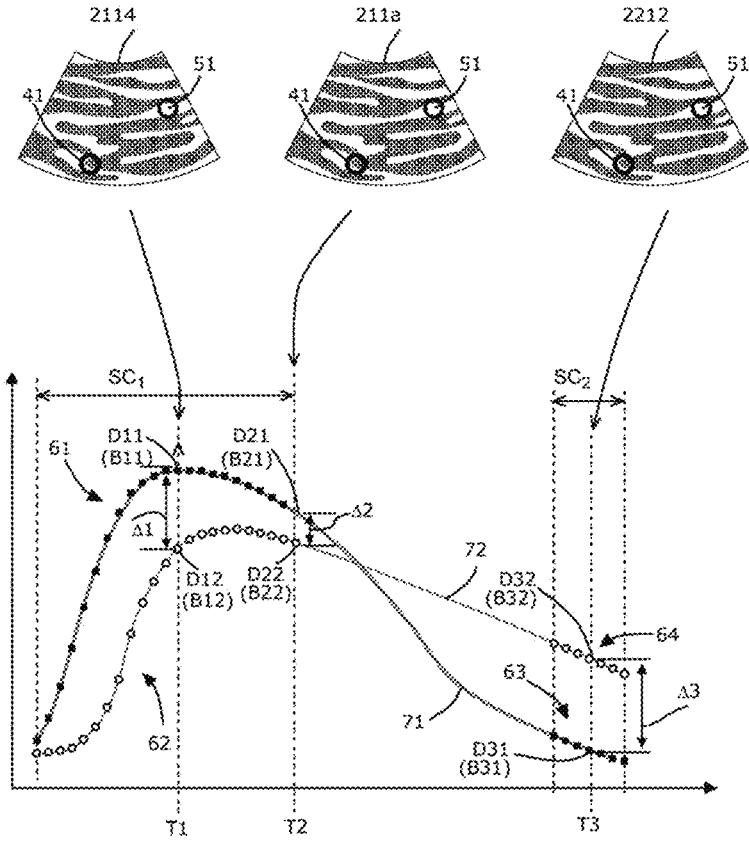
FIG. 13 is an explanatory diagram of the calculation method of the difference value according to an embodiment.

FIG. 13 is an explanatory diagram of the calculation method of the difference value.

The processor calculates the difference value $\Delta 1$ between the average luminance B11 of the region of interest 41 of the target in the contrast image 2114 of staining time phase T1 (in other words, the average luminance B11 represented by data D11) and the average luminance B12 of the region of interest 51 of the liver parenchyma (in other words, the average luminance B12 represented by data D12). When calculating the difference value $\Delta 1$, the difference value $\Delta 1$ (=B12−B11) may be calculated by subtracting the average luminance B11 of the region of interest 41 of the target from the average luminance B12 of the region of interest 51 of the liver parenchyma, or the difference value $\Delta 1$ (=B11−B12) may be calculated by subtracting the average luminance B12 of the region of interest 51 of the liver parenchyma from the average luminance B11 of the region of interest 41 of the target. In the present embodiment, the difference value $\Delta 1$ is calculated by subtracting the average luminance of the target region of interest 41 from the average luminance of the liver parenchyma region of interest 51. Thus, the processor calculates the difference value $\Delta 1$ (=B12−B11) by subtracting the average luminance B11 of the target region of interest 41 from the average luminance B12 of the liver parenchyma region of interest 51.

Furthermore, the processor calculates the difference value $\Delta 2$ between the average luminance B21 of the region of interest 41 of the target in the contrast image 211a of early phase T2 (in other words, the average luminance B21 represented by data D21) and the average luminance B22 of the region of interest 51 of the liver parenchyma (in other words, the average luminance B22 represented by data D22). When calculating the difference value $\Delta 2$, the difference value $\Delta 2$ (=B22−B21) may be calculated by subtracting the average luminance B21 of the region of interest 41 of the target from the average luminance B22 of the region of interest 51 of the liver parenchyma, or the difference value $\Delta 2$ (=B21−B22) may be calculated by subtracting the average luminance B22 of the region of interest 51 of the liver parenchyma from the average luminance B21 of the region of interest 41 of the target. In the present embodiment, the difference value $\Delta 2$ is calculated by subtracting the average luminance of the target region of interest 41 from the average luminance of the liver parenchyma region of interest 51, similar to the difference value $\Delta 1$. Thus, the processor calculates the difference value $\Delta 2$ (=B22−B21) by subtracting the average luminance B21 of the target region of interest 41 from the average luminance B22 of the liver parenchyma region of interest 51.

Furthermore, the processor calculates the difference value $\Delta 3$ between the average luminance B31 of the region of interest 41 of the target in the contrast image 2212 of late phase T3 (in other words, the average luminance B31 represented by data D31) and the average luminance B32 of the region of interest 51 of the liver parenchyma (in other words, the average luminance B32 represented by data D32). When calculating the difference value $\Delta 3$, the difference value $\Delta 3$ (=B32−B31) may be calculated by subtracting the average luminance B31 of the region of interest 41 of the target from the average luminance B32 of the region of interest 51 of the liver parenchyma, or the difference value $\Delta 3$ (=B31−B32) may be calculated by subtracting the average luminance B32 of the region of interest 51 of the liver parenchyma from the average luminance B31 of the region of interest 41 of the target. In the present embodiment, the difference value $\Delta 3$ is calculated by subtracting the average luminance of the target region of interest 41 from the average luminance of the liver parenchyma region of interest 51, similar to the difference value $\Delta 1$. Thus, the processor calculates the difference value $\Delta 3$ (=B32−B31) by subtracting the average luminance B31 of the target region of interest 41 from the average luminance B32 of the liver parenchyma region of interest 51.

After calculating difference values $\Delta 1$, $\Delta 2$, and $\Delta 3$, processing proceeds to step ST3.

In step ST3, the processor determines whether the difference values $\Delta 1$, $\Delta 2$, and $\Delta 3$ are all positive (or negative).

In staining time phase T1, the average luminance B12 of the liver parenchyma is smaller than the average luminance B11 of the target (B12<B11). Therefore, the difference value $\Delta 1 < 0$.

In the early phase T2, the average luminance B22 of the liver parenchyma is smaller than the average luminance B21 of the target (B22<B21). Therefore, the difference value $\Delta 2 < 0$.

On the other hand, in the late phase T3, the average luminance B32 of the liver parenchyma is larger than the average luminance B31 of the target (B32>B31). Therefore, the difference value $\Delta 3 > 0$.

Thus, the difference values $\Delta 1$ and $\Delta 2$ are negative, but the difference value $\Delta 3$ is positive. Therefore, it is determined that the difference values $\Delta 1$, $\Delta 2$, and $\Delta 3$ contain both positive difference values and negative difference values. If the difference values $\Delta 1$, $\Delta 2$, and $\Delta 3$ contain both positive and negative difference values, it means that in the early phase, the luminance of the target is greater than that of the liver parenchyma, but in the late phase, the target luminance is less than that of the liver parenchyma. Therefore, the brightness of the target is considered to be highly variable relative to the brightness of the liver parenchyma, indicating cases with good target staining. In cases with good target staining, the use of both data from the liver parenchyma and the target may provide useful information to determine if the contrast agent has been discharged from the target. Therefore, if the difference values Δ1, Δ2, and Δ3 contain both positive and negative difference values, the process proceeds to step ST4, and the processor determines to create a WO image using the data of the liver parenchyma and the target. The process then proceeds to step ST5.

Figure 14:
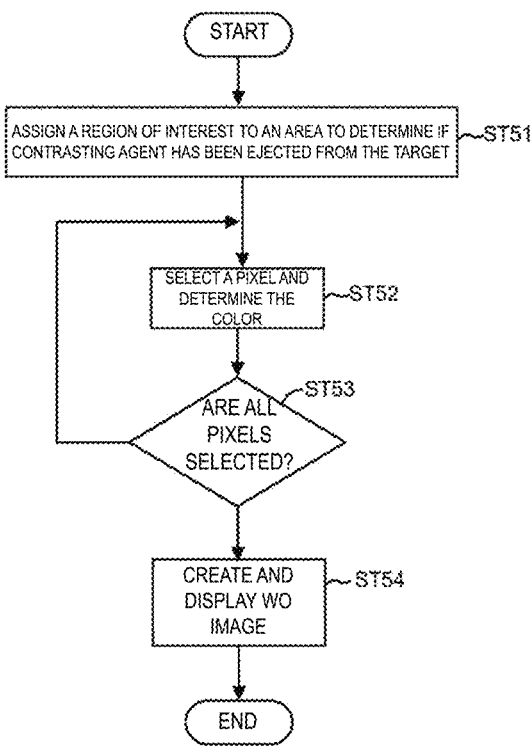
FIG. 14 is an explanatory diagram of a flowchart for creating the WO image in step ST5 according to an embodiment.

FIG. 14 is an explanatory diagram of a flowchart for creating the WO image in step ST5.

In step ST51, the user identifies the region in the body of the subject where there is need to determine whether the contrast agent has been discharged from the target, and assigns a region of interest to the identified region.

Figure 15:
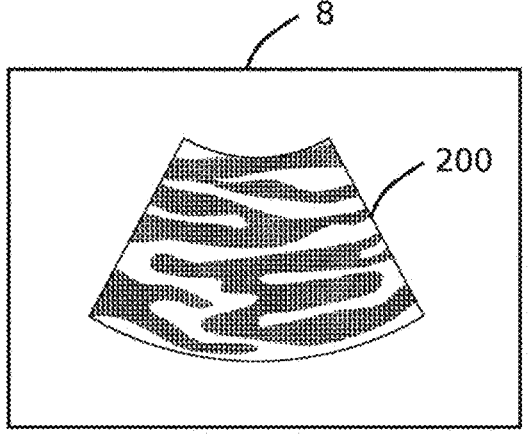
FIG. 15 is a diagram depicting a contrast image 200 displayed on the display unit according to an embodiment.
Figure 16:
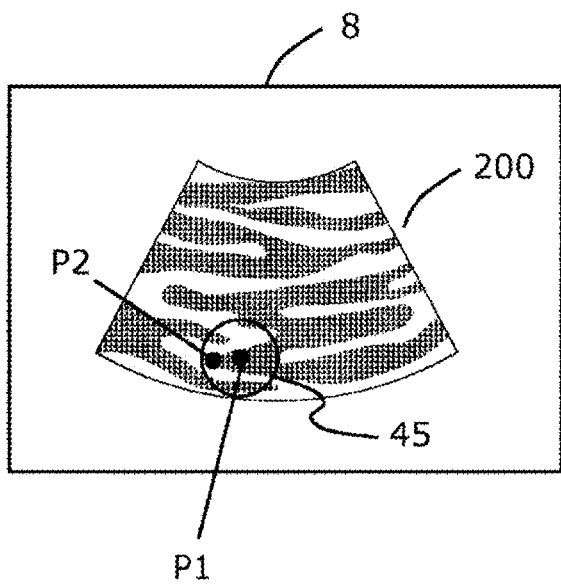
FIG. 16 is an explanatory diagram of the region of interest 45 according to an embodiment.

FIGS. 15 and 16 depict how to assign a region of interest to the region where there is a need to determine if the contrast agent has been discharged from the target.

The user operates the user interface 10 and enters a command to display the contrast image 200. When the user interface 10 accepts the user input to display the contrast image 200, the contrast image 200 is displayed on the display unit 8, as depicted in FIG. 15. The contrast image 200 can be selected, for example, from the contrast images 2111 to 211a included in image group 21 (or from contrast images 2211 to 221b included in image group 22). Furthermore, a contrast image may be selected from the three contrast images selected in step ST1 (contrast image 2114 of the staining time phase T1, contrast image 211a of the early phase, and contrast image 2212 of the late phase). After selecting the contrast image 200, the user assigns a region of interest to the contrast image 200 at the point where the user wants to check the timing of the discharge of the contrast agent.

FIG. 16 is an explanatory diagram of the region of interest 45.

The user operates the user interface 10 and enters an instruction to assign a region of interest 45 to the location (for example, the target) where the user wants to check the timing of discharging the contrast agent. When the user interface 10 accepts the user input to assign a region of interest 45, the processor assigns a region of interest 45 to the contrast image 200. The region of interest 45 is, for example, the region containing the target. Once the contrast image 200 has been assigned a region of interest 45, the process proceeds to step ST52.

In step ST52, the processor selects pixels from the region of interest 45 and determines the color to assign to the selected pixels. Here, an example of assigning the color of pixel P1 in the region of interest 45 is described.

Figure 17:
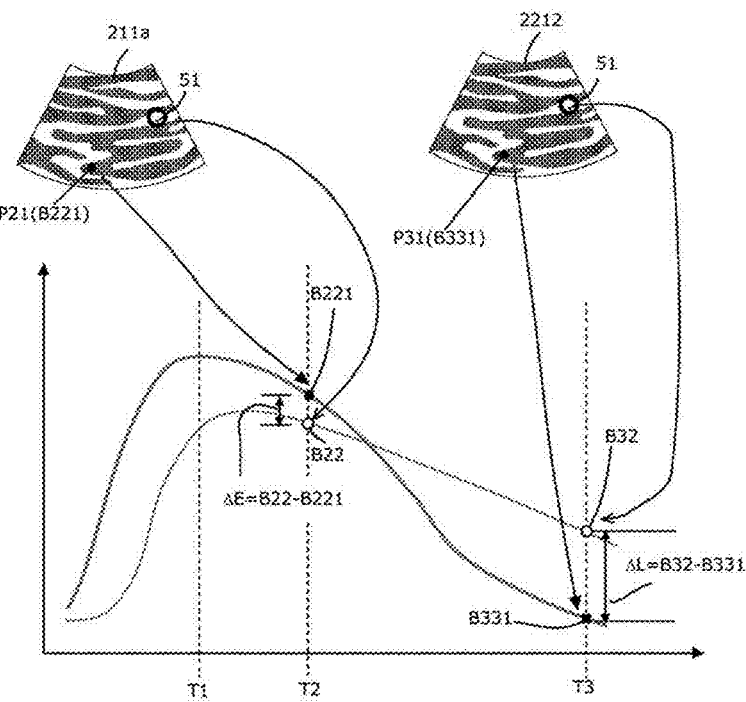
FIG. 17 is an explanatory diagram of the procedure for determining the color to be assigned to pixel P1 in the region of interest 45 according to an embodiment.
Figure 18:
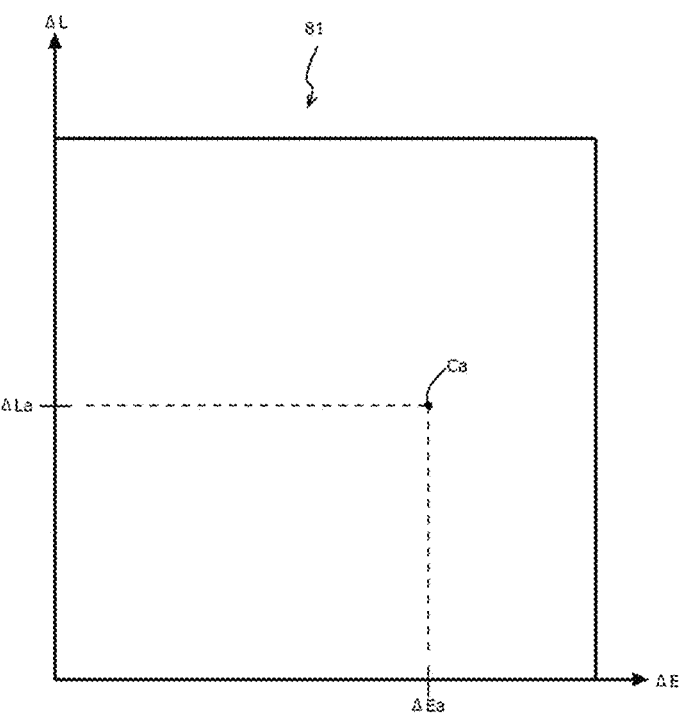
FIG. 18 is an explanatory diagram of the color map 81 according to an embodiment.

FIG. 17 is an explanatory diagram of the procedure for determining the color to be assigned to pixel P1 in the region of interest 45.

The processor reads from memory the average luminance B22 of the liver parenchyma (region of interest 51) of the contrast image 211a in the early phase T2. Furthermore, the processor also reads the luminance value B221 of pixel P21 from the contrast image 211a in the early phase T2. This pixel P21 corresponds to pixel P1 in the region of interest 45 of the contrast image 200. The processor then calculates the difference value ΔE between the average luminance B22 of the liver parenchyma and the luminance value B221 of pixel P21. When calculating the difference value ΔE, the difference value ΔE (=B22−B221) may be calculated by subtracting the luminance value B221 of pixel P21 from the average luminance B22 of the liver parenchyma, or by calculating the difference value ΔE (=B221−B22) by subtracting the average luminance B22 of the liver parenchyma from the luminance value B221 of pixel P21. In the present embodiment, the difference value ΔE is calculated by subtracting the pixel's luminance value from the average luminance of the liver parenchyma. Thus, the processor calculates the difference value ΔE (=B22−B221) by subtracting the luminance value B221 of pixel P21 from the average luminance B22 of the liver parenchyma.

Furthermore, the processor also reads from memory the average luminance B32 of the liver parenchyma (region of interest 51) of the contrast image 2212 in the late phase T3, and the luminance value B331 of pixel P31 of the contrast image 2212 in the late phase T3. This pixel P31 corresponds to pixel P1 in the region of interest 45 of the contrast image 200. Furthermore, the processor then calculates the difference value ΔL between the average luminance B32 of the liver parenchyma and the luminance value B331 of pixel P31. When calculating the difference value ΔL, the difference value ΔL (=B32−B331) may be calculated by subtracting the luminance value B331 of pixel P31 from the average luminance B32 of the liver parenchyma, or by calculating the difference value ΔL (=B331−B32) by subtracting the average luminance B32 of the liver parenchyma from the luminance value B331 of pixel P31. In the present embodiment, the difference value ΔL is calculated by subtracting the pixel luminance value from the average luminance of the liver parenchyma, similar to the difference value ΔE. Thus, the processor calculates the difference value ΔL (=B32−B331) by subtracting the luminance value B331 of pixel P31 from the average luminance B32 of the liver parenchyma.

The processor then determines the color to be assigned to pixel P1 (see FIG. 16) in the region of interest 45 based on the combination of these two difference values ΔE (=B22−B221) and ΔL (=B32−B331).

FIGS. 18 through 21 depict how to determine the color to be assigned to pixel P1 in the region of interest 45 based on the two difference values ΔE and ΔL.

The processor determines the color to assign to pixel P1 from the color map 81 based on the two difference values ΔE and ΔL.

The color map 81 is stored in memory. The horizontal axis of color map 81 represents the difference value ΔE in the early phase T2, and the vertical axis represents the difference value ΔL in the late phase T3. The difference values ΔE and ΔL may have negative values, but if the difference values ΔE and ΔL are negative, the values are considered "zero" on the color map 81.

Figure 19:
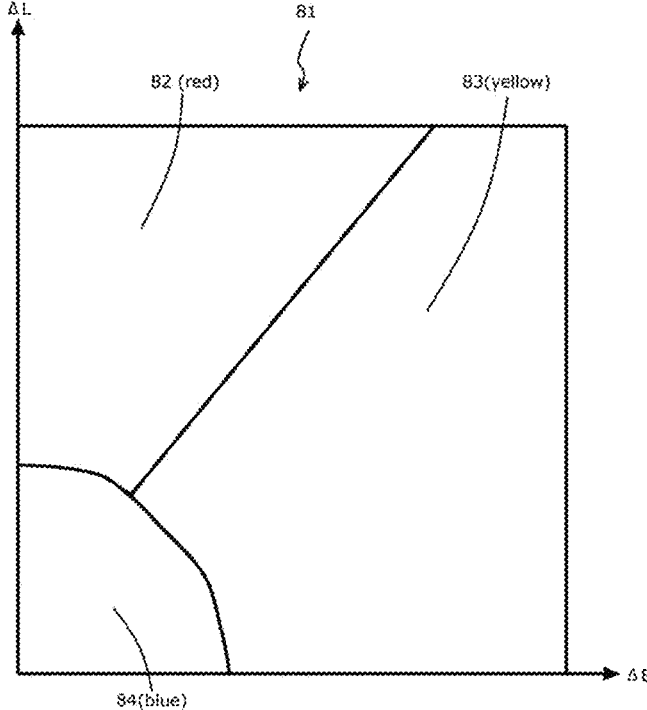
FIG. 19 is a diagram depicting the three regions 82, 83, and 84 of the color map 81 according to an embodiment.

The colormap 81 represents the color determined by the combination of the two difference values ΔE and ΔL. For example, if the difference value ΔE is ΔE=ΔEa and the difference value ΔL is ΔL=ΔLa, the color determined by this combination of difference values is Ca. Thus, the color can be determined by a combination of the two difference values ΔE and ΔL. Although the color map 81 can determine thousands to tens of thousands of colors depending on the combination of the two difference values ΔE and ΔL, here, for convenience of description, the area of the color map 81 is divided into three regions 82, 83, and 84, as depicted in FIG. 19, and the regions 82, 83, and 84 are respectively assigned to be red, yellow, and blue.

Thus, in the present embodiment, each pixel in the region of interest 45 is assigned a color selected from red, yellow, and blue.

Returning to FIG. 17, the difference value ΔE in the early phase T2 is ΔE=B22−B221, and the difference value ΔL in late phase T3 is ΔL=B32−B331. Thus, the processor determines the color to be assigned to pixel P1 by a combination of the difference value ΔE=B22−B221 and the difference value ΔL=B32−B331.

Figure 20:
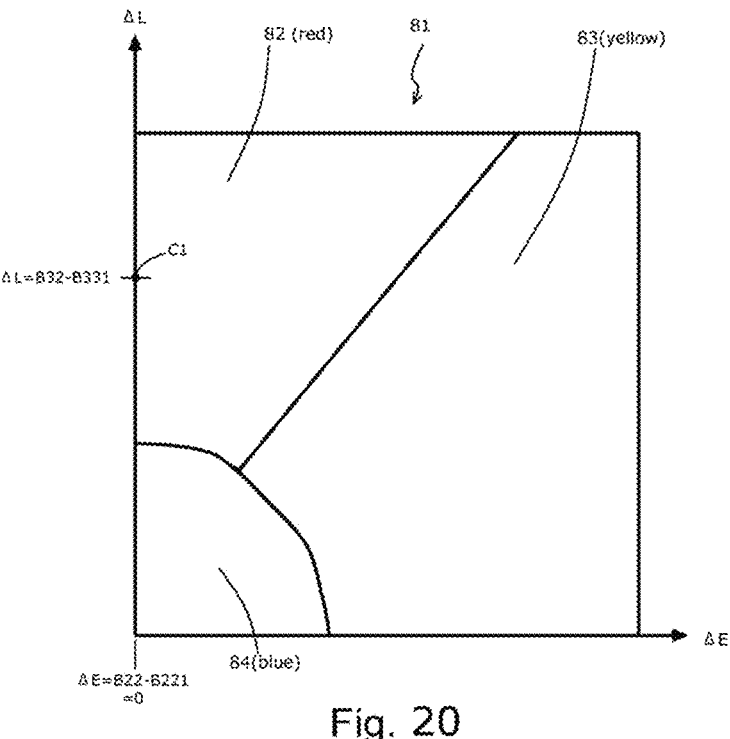
FIG. 20 is an explanatory diagram depicting when the color is determined by the difference value $\Delta E=B22-B221$ and the difference value $\Delta L=B32-B331$ according to an embodiment.

FIG. 20 is an explanatory diagram depicting when the color is determined by the difference value $\Delta E=B22-B221$ and the difference value $\Delta L=B32-B331$.

The difference value $\Delta E$ for the early phase T2 is $\Delta E=B22-B221$. Herein, $B22<B221$ (see FIG. 17). Therefore, since $\Delta E=B22-B221$ is negative, the processor determines that $\Delta E=B22-B221$ is "zero".

On the other hand, the difference value $\Delta L$ of the late phase T3 is $\Delta L=B32-B331$. Here, since $B32>B331$ (see FIG. 17), $\Delta L=B32-B331$ is positive. Thus, the processor identifies the point $(B32-B331)$ from the axis $\Delta L$.

Therefore, the processor can identify the color C1 corresponding to the combination of the difference value $\Delta E=B22-B221$ and the difference value $\Delta L=B32-B331$ from the color map 81. Color C1 is included in region 82, so color C1 represents red. Thus, the processor assigns red as the color at pixel P1 in the region of interest 45. After determining the color to be assigned, the process proceeds to step ST53.

In step ST53, the processor determines whether all pixels from the region of interest 45 have been selected. Here, again, only pixel P1 is selected, so the process returns to step ST52.

Furthermore, the processor then determines the color to be assigned for the other pixels in the same manner.

Figure 21:
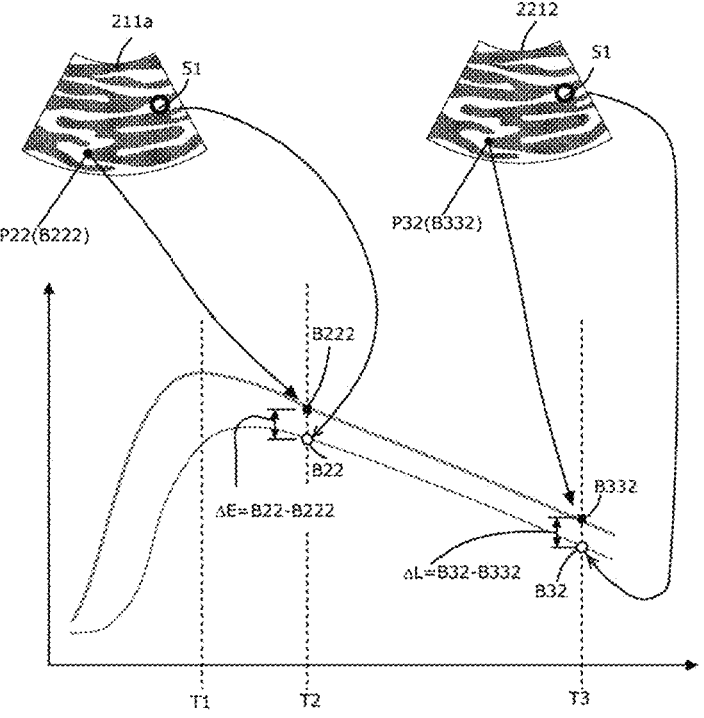
FIG. 21 is an explanatory diagram when determining the color to be assigned to pixel P2 in the region of interest 45 according to an embodiment.

FIG. 21 is an explanatory diagram when determining the color to be assigned to pixel P2 in the region of interest 45.

The processor reads from memory the average luminance B22 of the liver parenchyma (region of interest 51) of the contrast image 211*a* in the early phase T2. Furthermore, the processor also reads the luminance value B222 of pixel P22 from the contrast image 211*a* in the early phase T2. This pixel P22 corresponds to pixel P2 (See FIG. 16) in the region of interest 45 of the contrast image 200. Furthermore, the processor calculates the difference value $\Delta E$ $(=B22-B222)$ by subtracting the luminance value B222 of pixel P22 from the average luminance B22 of the liver parenchyma.

Furthermore, the processor also reads from memory the average luminance B32 of the liver parenchyma (region of interest 51) of the contrast image 2212 in the late phase T3, and the luminance value B332 of pixel P32 of the contrast image 2212 in the late phase T3. This pixel P32 corresponds to pixel P2 in the region of interest 45 of the contrast image 200. Furthermore, the processor calculates the difference value $\Delta L$ $(=B32-B332)$ by subtracting the luminance value B332 of pixel P32 from the average luminance B32 of the liver parenchyma.

Thus, two difference values $\Delta E$ $(=B22-B222)$ and a difference value $\Delta L$ $(=B32-B332)$ can be calculated.

After calculating the two difference values $\Delta E$ and $\Delta L$, the processor determines the color to assign to pixel P2 (see FIG. 16) in the region of interest 45 based on these two difference values $\Delta E$ $(=B22-B222)$ and $\Delta L$ $(=B32-B332)$.

Figure 22:
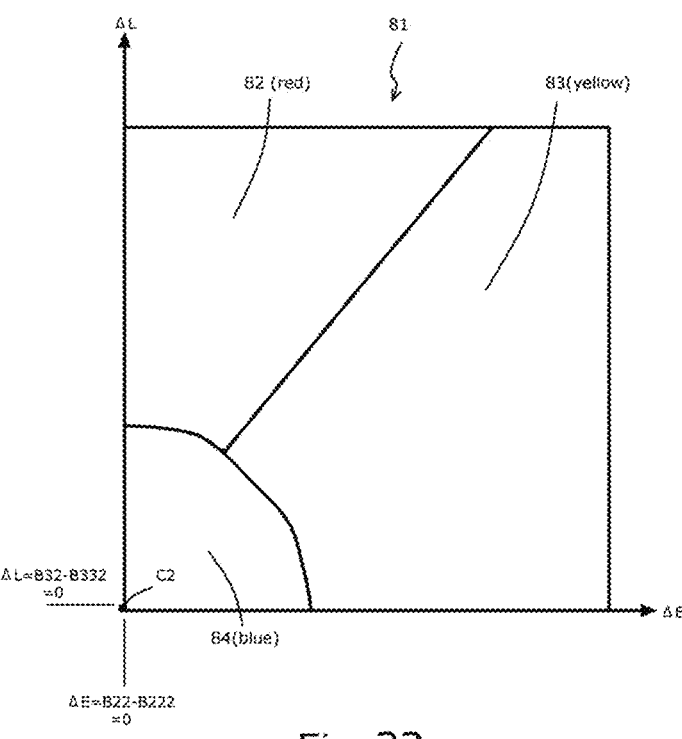
FIG. 22 is a diagram depicting when the color is determined by the difference value $\Delta E=B22-B222$ and the difference value $\Delta L=B32-B332$ according to an embodiment.

FIG. 22 is an explanatory diagram depicting when color is determined by the difference value $\Delta E=B22-B222$ and the difference value $\Delta L=B32-B332$.

The difference value $\Delta E$ for the early phase T2 is $\Delta E=B22-B222$. Herein, $B22<B222$ (see FIG. 21). Therefore, since $\Delta E=B22-B222$ is negative, the processor determines that $\Delta E=B22-B222$ is "zero".

Furthermore, the difference value $\Delta L$ of the late phase T3 is $\Delta L=B32-B332$. Here, since $B32<B3322$ (see FIG. 21), $\Delta L=B32-B332$ is positive. Therefore, the processor determines that $\Delta L=B32-B332$ is "zero".

Therefore, the processor can identify the color C2 corresponding to the combination of the difference value $\Delta E=B22-B222$ and the difference value $\Delta L=B32-B332$ from the color map 81. Color C2 is included in region 84, so color C2 represents blue. Thus, the processor assigns blue as the color at pixel P2 in the region of interest 45. After determining the color to be assigned, the process proceeds to step ST53.

In step ST53, the processor determines whether all pixels from the region of interest 45 have been selected. Here, only pixels P1 and P2 have been selected, so the process returns to step ST52.

In the same manner, the processor determines the color to assign to other pixels based on the combination of the two difference values $\Delta E$ and $\Delta L$.

Figure 23:
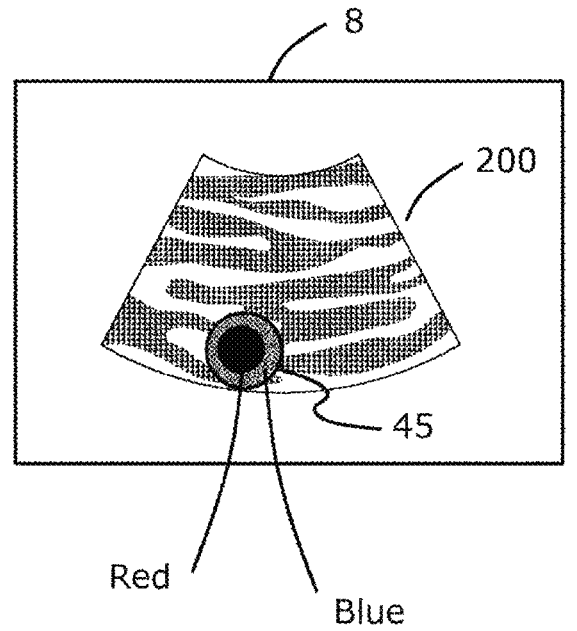
FIG. 23 is a schematic diagram depicting the WO image according to an embodiment.

Thus, a color can be assigned to each pixel within the region of interest 45. If it is determined that all pixels have been selected in step ST53, the process proceeds to step ST54 to create and display the WO image. FIG. 23 is a schematic diagram depicting the WO image.

FIG. 23 depicts an example of target luminance decreasing in the late phase (contrast agent being discharged). Once the WO image is displayed, the flow in FIG. 5 is completed.

The WO image can be color-coded to indicate when the contrast agent is discharged. Therefore, the user can easily visually recognize when the luminance of the target decreases by viewing the WO image.

The above example describes a case with good target staining. Next, the case of poor target staining is described with reference to the flow in FIG. 5.

In step ST1, similar to the previously described method, contrast images in the staining time phase T1, early phase T2, and late phase T3 are selected and assigned regions of interest.

Figure 24:
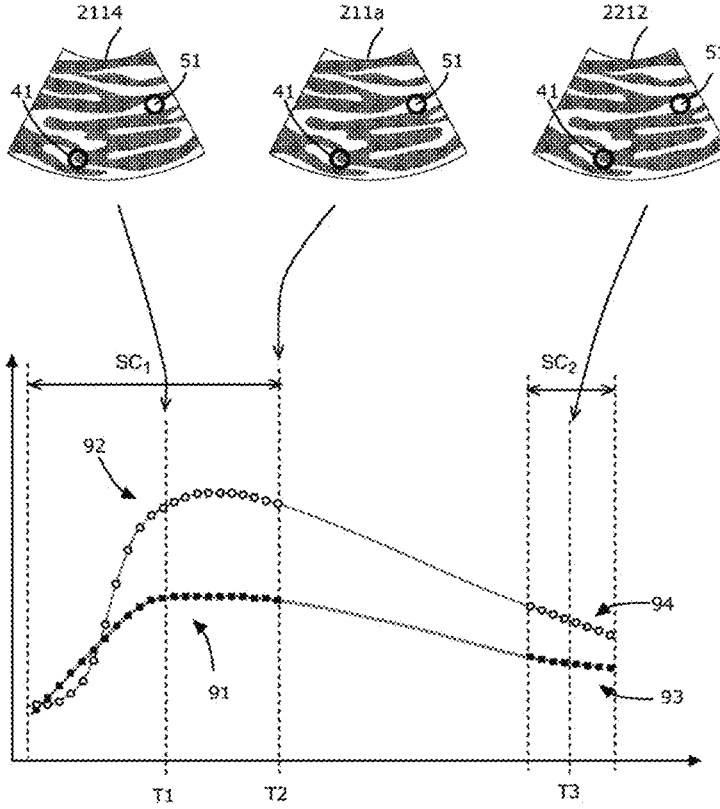
FIG. 24 is an explanatory diagram of step ST1 according to an embodiment.

FIG. 24 is an explanatory diagram of step ST1.

The processor selects the contrast image 2114 of the staining time phase T1, the contrast image 211*a* of the early phase T2, and the contrast image 2212 of the late phase T3. Furthermore, regions of interest 41 and 51 are assigned, and data groups 91 and 93 representing the temporal change in average luminance at the target and data groups 92 and 94 representing the temporal change in average luminance at the liver parenchyma are obtained.

Data group 91 represents the data group of targets acquired during data acquisition period SC1, and data group 93 represents the data group of targets acquired during data acquisition period SC2. Furthermore, data group 92 represents the data group of the liver parenchyma acquired during data acquisition period SC1, and data group 94 represents the data group of the liver parenchyma acquired during data acquisition period SC2. FIG. 24 represents a case of poor target staining and depicts an example where the average brightness of the target is lower than the average brightness of the liver parenchyma over staining time phases T1, early phase T2, and late phase T3.

Once the average luminance of the target and liver parenchyma in the staining time phases T1, early phase T2, and late phase T3 have been determined, the process proceeds to step ST2.

In step ST2, the processor determines the major/minor relationship between the average luminance of the target and the average luminance of the liver parenchyma for each of the staining time phases T1, early phase T2, and late phase T3. In the present embodiment, the case in which the difference value between the average luminance of the target and the average luminance of the liver parenchyma is calculated as the major/minor relationship between the average luminance of the target and the average luminance of the liver parenchyma is described.

Figure 25:
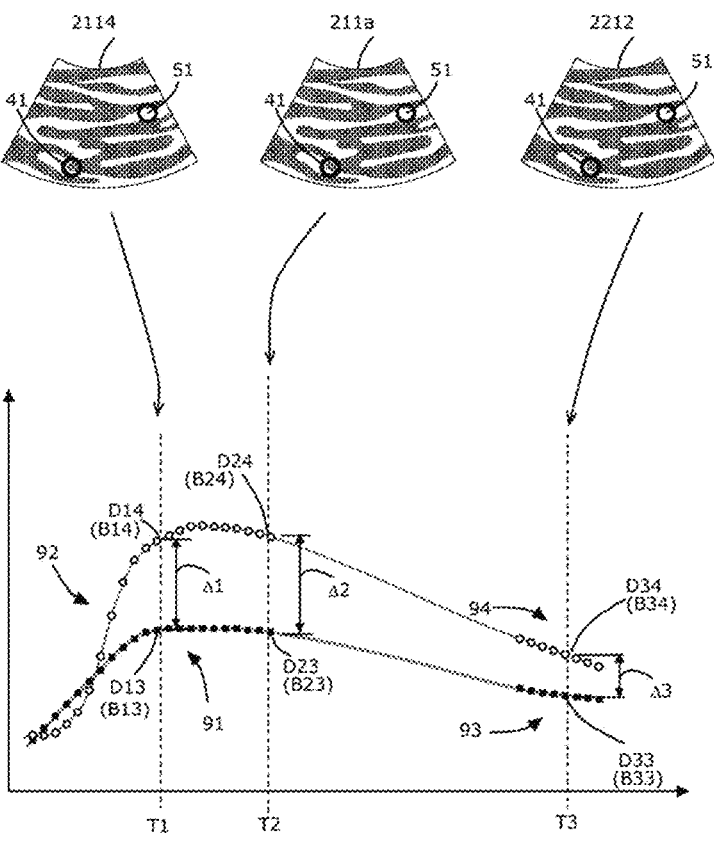
FIG. 25 is an explanatory diagram of the calculation method of the difference value according to an embodiment.

FIG. 25 is an explanatory diagram of the calculation method of the difference value.

The processor calculates the difference value $\Delta 1$ between the average luminance B13 of the region of interest 41 of the target in the contrast image 2114 of staining time phase T1 (in other words, the average luminance B13 represented by data D13) and the average luminance B13 of the region of interest 51 of the liver parenchyma (in other words, the average luminance B14 represented by data D14). When calculating the difference value $\Delta 1$, the difference value $\Delta 1$ (=B14−B13) may be calculated by subtracting the average luminance B13 of the region of interest 41 of the target from the average luminance B14 of the region of interest 51 of the liver parenchyma, or the difference value $\Delta 1$ (=B13−B14) may be calculated by subtracting the average luminance B14 of the region of interest 51 of the liver parenchyma from the average luminance B13 of the region of interest 41 of the target. In the present embodiment, the difference value $\Delta 1$ is calculated by subtracting the average luminance of the target region of interest 41 from the average luminance of the liver parenchyma region of interest 51. Thus, the processor calculates the difference value $\Delta 1$ (=B14−B13) by subtracting the average luminance B13 of the target region of interest 41 from the average luminance B14 of the liver parenchyma region of interest 51.

Furthermore, the processor calculates the difference value $\Delta 2$ between the average luminance B23 of the region of interest 41 of the target in the contrast image 211$a$ of early phase T2 (in other words, the average luminance B23 represented by data D23) and the average luminance B24 of the region of interest 51 of the liver parenchyma (in other words, the average luminance B24 represented by data D24). When calculating the difference value $\Delta 2$, the difference value $\Delta 2$ (=B24−B23) may be calculated by subtracting the average luminance B23 of the region of interest 41 of the target from the average luminance B24 of the region of interest 51 of the liver parenchyma, or the difference value $\Delta 2$ (=B23−B24) may be calculated by subtracting the average luminance B24 of the region of interest 51 of the liver parenchyma from the average luminance B23 of the region of interest 41 of the target. In the present embodiment, the difference value $\Delta 2$ is calculated by subtracting the average luminance of the target region of interest 41 from the average luminance of the liver parenchyma region of interest 51, similar to the difference value $\Delta 1$. Thus, the processor calculates the difference value $\Delta 2$ (=B24−B23) by subtracting the average luminance B23 of the target region of interest 41 from the average luminance B24 of the liver parenchyma region of interest 51.

Furthermore, the processor calculates the difference value $\Delta 3$ between the average luminance B33 of the region of interest 41 of the target in the contrast image 2212 of late phase T3 (in other words, the average luminance B33 represented by data D33) and the average luminance B34 of the region of interest 51 of the liver parenchyma (in other words, the average luminance B34 represented by data D34). When calculating the difference value $\Delta 3$, the difference value $\Delta 3$ (=B34−B33) may be calculated by subtracting the average luminance B33 of the region of interest 41 of the target from the average luminance B34 of the region of interest 51 of the liver parenchyma, or the difference value $\Delta 3$ (=B33−B34) may be calculated by subtracting the average luminance B34 of the region of interest 51 of the liver parenchyma from the average luminance B33 of the region of interest 41 of the target. In the present embodiment, the difference value $\Delta 3$ is calculated by subtracting the average luminance of the target region of interest 41 from the average luminance of the liver parenchyma region of interest 51, similar to the difference value $\Delta 1$. Thus, the processor calculates the difference value $\Delta 3$ (=B34−B33) by subtracting the average luminance B33 of the target region of interest 41 from the average luminance B34 of the liver parenchyma region of interest 51.

After calculating difference values $\Delta 1$, $\Delta 2$, and $\Delta 3$, processing proceeds to step ST3.

In step ST3, the processor determines whether the difference values $\Delta 1$, $\Delta 2$, and $\Delta 3$ are all positive (or negative).

In the staining time phase T1, the average luminance B14 of the liver parenchyma is larger than the average luminance B13 of the target (B14>B13). Therefore, the difference value $\Delta 1$>0.

In the early phase T2, the average luminance B24 of the liver parenchyma is larger than the average luminance B23 of the target (B24>B23). Therefore, the difference value $\Delta 2$>0.

In the late phase T3, the average luminance B34 of the liver parenchyma is larger than the average luminance B33 of the target (B34>B33). Therefore, the difference value $\Delta 3$>0.

Thus, the three difference values $\Delta 1$, $\Delta 2$, and $\Delta 3$ are all positive. Therefore, the difference values $\Delta 1$, $\Delta 2$, and $\Delta 3$ are all determined to be positive. If the difference values $\Delta 1$, $\Delta 2$, and $\Delta 3$ are all positive, the target is considered to be not sufficiently stained. In this case, if an attempt is made to obtain a WO image using the difference values between the target and the liver parenchyma, as in cases with good target staining, obtaining a suitable WO image will be difficult because it is difficult to see a significant difference between the difference values between the target and the liver parenchyma in the early phase and the difference values between the target and the liver parenchyma in the late phase. Therefore, if all the difference values $\Delta 1$, $\Delta 2$, and $\Delta 3$ are determined to be positive (or negative), the processor determines to proceed to step ST6 and create a WO image based on the time variation of the luminance (characteristic value) of the target, instead of using the difference values between the target and the liver parenchyma. The process then proceeds to step ST5. Step ST5 will be described below with reference to the flow of FIG. 14.

Figure 26:
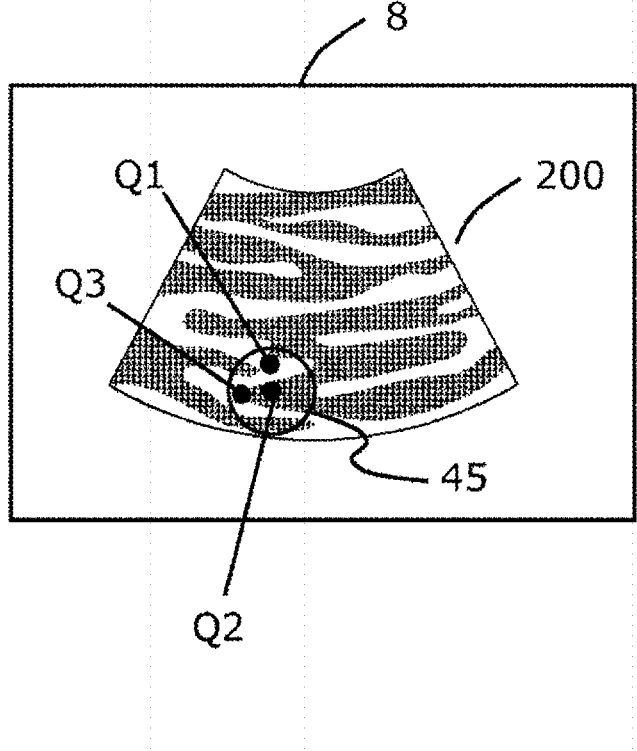
FIG. 26 is a diagram depicting a region of interest 45 assigned in the contrast image 200 according to an embodiment.

In step ST51, the user displays the contrast image 200 on the display unit 8 and assigns a region of interest 45 in the contrast image 200, as depicted in FIG. 26. Once the contrast image 200 has been assigned a region of interest 45, the process proceeds to step ST52.

In step ST52, the processor determines the color to be assigned to each pixel of the region of interest 45. Step ST52 is described below.

In step ST52, the processor selects pixels from the region of interest 45 and determines the color to assign to the selected pixels. Here, an example of assigning the color of pixel Q1 in the region of interest 45 is described.

Figure 27:
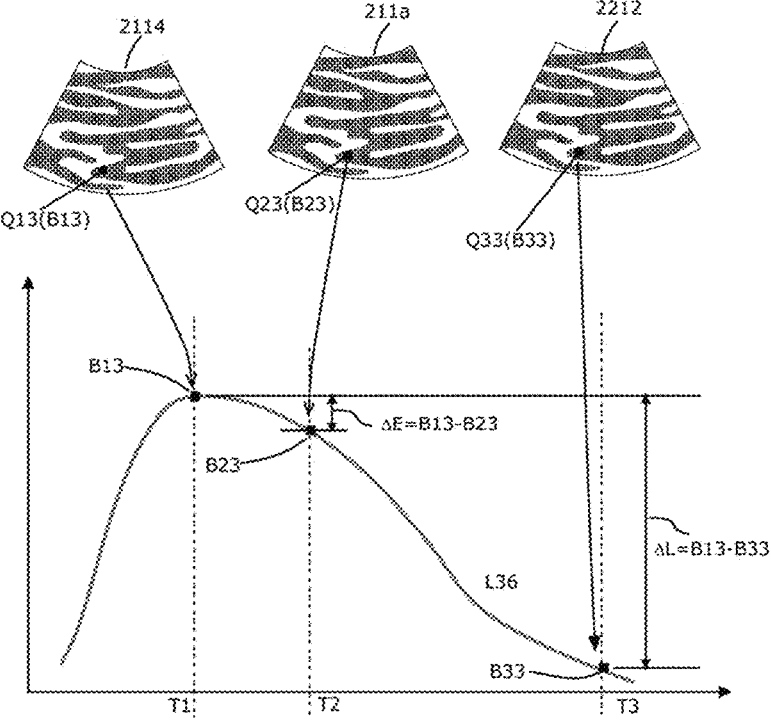
FIG. 27 is an explanatory diagram of a method of determining the assigned color according to an embodiment.

FIG. 27 is an explanatory diagram of a method of determining the assigned color.

The processor reads the luminance value B13 of pixel Q13 from the contrast image 2114 at the staining time phase T1. This pixel Q13 corresponds to pixel Q1 in the region of interest 45 of the contrast image 200.

Furthermore, the processor also reads the luminance value B23 of pixel Q23 from the contrast image 211$a$ in the early phase T2. This pixel Q23 corresponds to pixel Q1 in the region of interest 45 of the contrast image 200.

The processor calculates the difference value $\Delta E$ between the luminance value B13 of the staining time phase T1 and the luminance value B23 of the early phase T2. When calculating the difference value ΔE, the difference value ΔE (=B13−B23) may be calculated by subtracting the luminance value B23 of the early phase T2 from the luminance value B13 of the staining time phase T1, or the difference value ΔE (=B23−B13) may be calculated by substracting the luminance value B13 of the early phase T2 from the luminance value B23 of the staining time phase T1. In the present embodiment, the difference value ΔE is calculated by subtracting the luminance value of the early phase T2 from the luminance value of staining time phase T1. Therefore, the processor calculates the difference value ΔE (=B13−B23) by subtracting the luminance value B23 of the early phase T2 from the luminance value B13 of the staining time phase T1.

Furthermore, the processor reads the luminance value B33 of the pixel Q33 from the contrast image 2212 of the late phase T3. This pixel Q33 corresponds to pixel Q1 in the region of interest 45 of the contrast image 200. Furthermore, the processor calculates the difference value ΔL between the luminance value B13 of the staining time phase T1 and the luminance value B33 of the late phase T3. When calculating the difference value ΔL, the difference value ΔL (=B13−B33) may be calculated by subtracting the luminance value B33 of the late phase T3 from the luminance value B13 of the staining time phase T1, or the difference value ΔL (=B33−B13) may be calculated by subtracting the luminance value B13 of the late phase T3 from the luminance value B33 of the staining time phase T1. In the present embodiment, the difference value ΔL is calculated by subtracting the luminance value of the late phase T3 from the luminance value of staining time phase T1. Therefore, the processor calculates the difference value ΔL (=B13−B33) by subtracting the luminance value B33 of the late phase T3 from the luminance value B13 of the staining time phase T1.

The processor then determines the color to be assigned to pixel Q1 (see FIG. 26) in the region of interest 45 based on the combination of these two difference values ΔE (=B13−B23) and ΔL (=B13−B33).

Figure 28:
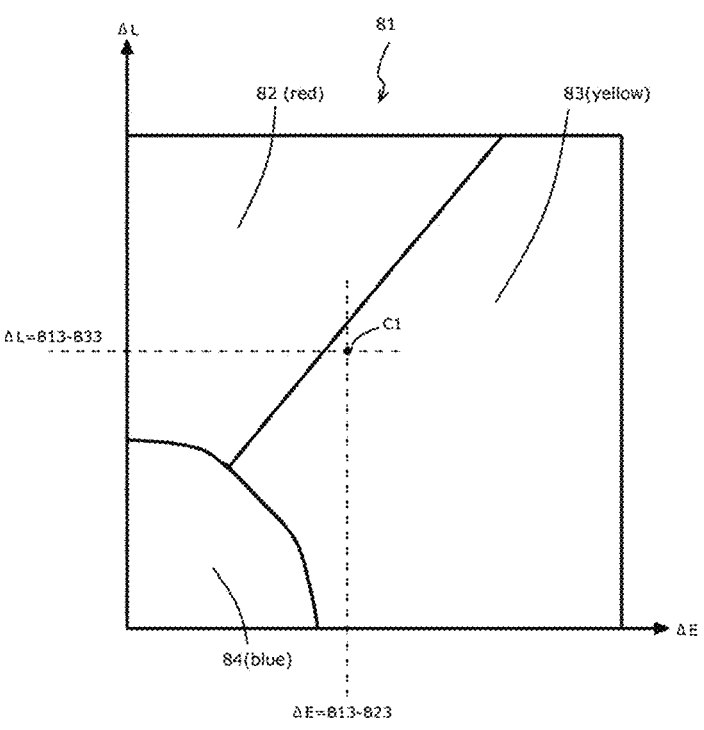
FIG. 28 is an explanatory diagram when the color to be assigned to pixel Q1 is determined based on two difference values $\Delta E$ $(=B13-B23)$ and $\Delta L$ $(=B13-B33)$ according to an embodiment.

FIG. 28 is an explanatory diagram when the color to be assigned to pixel Q1 is determined based on two difference values ΔE (=B13−B23) and ΔL (=B13−B33).

The processor determines the color to assign to pixel Q1 from the color map 81 based on the two difference values ΔE and ΔL.

The color map 81 is stored in memory. The horizontal axis of the color map 81 represents the difference value ΔE between staining time phase T1 and early phase T2, and the vertical axis represents the difference value ΔL between staining time phase T1 and late phase T3. Although the color map 81 can determine thousands to tens of thousands of colors depending on the combination of the two difference values ΔE and ΔL, here, for convenience of description, the area of the color map 81 is divided into three regions 82, 83, and 84, as depicted in FIG. 28, and the regions 82, 83, and 84 are respectively assigned to be red, yellow, and blue.

Thus, in the present embodiment, each pixel in the region of interest 45 is assigned a color selected from red, yellow, and blue.

As depicted in FIG. 27, the difference value ΔE between the staining time phase T1 and the early phase T2 is ΔE=B13−B23, and the difference value ΔL between staining time phase T1 and late phase T3 is ΔL=B13−B33. Therefore, the processor can identify the color C1 corresponding to the combination of the difference value ΔE=B13−B23 and the difference value ΔL=B13−B33 from the color map 81. Color C1 is included in region 83, so color C1 represents yellow. Thus, the processor assigns yellow as the color at pixel Q1 in the region of interest 45. After determining the color to be assigned, the process proceeds to step ST53.

In step ST53, the processor determines whether all pixels from the region of interest 45 have been selected. Here, only pixel Q1 is selected, so the process returns to step ST52 to assign the color of each pixel in the same manner.

Figure 29:
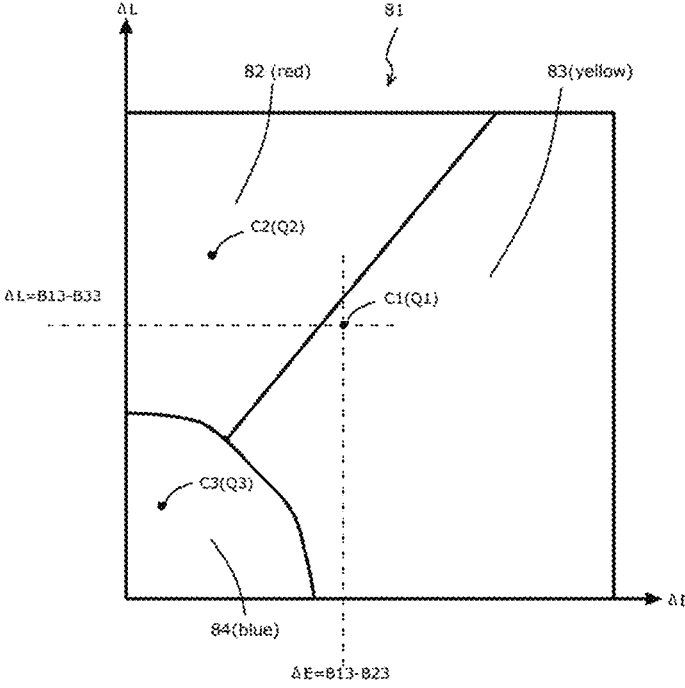
FIG. 29 is an explanatory diagram of the colors assigned to pixels Q2 and Q3 according to an embodiment.

FIG. 29 depicts as other pixels, color C2, which is assigned to pixel Q2, and color C3, which is assigned to pixel Q3. Color C2 is red and color C3 is blue.

In the same manner, the processor determines the color to assign to other pixels based on the combination of the two difference values ΔE and ΔL.

Figure 30:
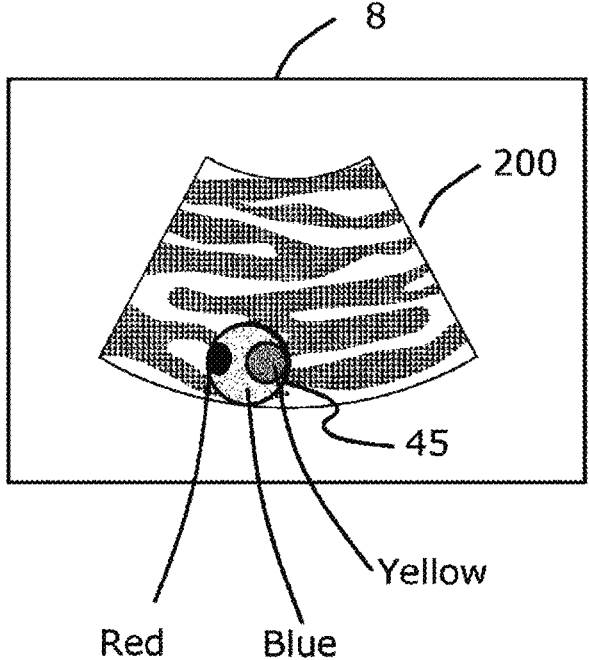
FIG. 30 is a schematic diagram depicting the WO image according to an embodiment.

Thus, a color can be assigned to each pixel within the region of interest 45. If it is determined that all pixels have been selected in step ST53, the process proceeds to step ST54 to create and display the WO image. FIG. 30 is a schematic diagram depicting the WO image. FIG. 30 depicts an example of luminance reduction of the target in the early phase.

The WO image can be created in this manner.

With the present embodiment, in cases with good target staining, the WO image is created using both the data from the target and the liver parenchyma (using the difference values between the liver parenchyma and the target). On the other hand, if target staining is poor, if an attempt is made to obtain a high quality WO image using both the data of the target and the data of the liver parenchyma, similar to cases with good target staining, obtaining a suitable WO image will be difficult because it is difficult to see a significant difference between the difference values between the target and the liver parenchyma in the early phase and the difference values between the target and the liver parenchyma in the late phase. Therefore, in cases with poor target staining, the WO image is created using only the luminance of the target, without using the luminance of the liver parenchyma. Thus, even in cases with poor target staining, WO images can be obtained that are suitable for determining at what time phase the contrast agent was discharged from the target.

In cases where the target is well stained, the color assigned to the pixel is determined based on the difference value in the early phase and the difference value in the late phase. Therefore, colors are assigned based not only on the difference values in the early phase (or late phase), but also on the difference values in both the early and late phases, so that colors can be determined reflecting the information in both the early and late phases of time, and thus high-quality WO images can be obtained.

Although the WO images were created based on the contrast images of the staining time phase T1, the early phase T2, and the late phase T3, the WO images may be created using contrast images of other time phases instead of the contrast images of these time phases.

Furthermore with the present embodiment, the contrast image of the time phase when the luminance of the target is at a peak is selected as the contrast image of the staining time phase T1. However, if it is possible to select a contrast image of a time phase in which the target is sufficiently stained with contrast agent, the contrast image of staining time phase T1 is not necessarily limited to the contrast image of the peak time phase, and a contrast image of a time phase off the peak may be selected as the contrast image of the staining time phase. For example, the contrast image of the time phase when the difference between the luminance of the target and the luminance of the liver parenchyma is maximum may be selected as the contrast image of staining time phase T1.

Furthermore, with this embodiment, the contrast image at about 5 minutes after the contrast agent was administered is selected as the contrast image of the late phase T3. However, the contrast image of the late phase T3 is not limited to the contrast image at about 5 minutes after the contrast agent is administered. For example, a contrast image at about 10 minutes after the contrast agent is administered may be selected as the contrast image for the late phase T3.

REFERENCE SIGNS LIST

1. Ultrasonic diagnostic device
2. Ultrasonic probe
2a Vibrating element
3. Transmission beamformer
4. Transmitter
5. Receiver
6. Reception beamformer
7. Processor
8. Display unit
9. Memory
10. User interface
20. Thumbnail region
21, 22, 23, 2n. Image group
40. Image display region
41, 42, 43, 44, 45, 51, 53. Region of interest
56. Operator
57. Subject
60. TIC region
61, 62, 63, 64, Data group
71, 72, Time intensity curve
81. Color Map
82, 83, 84. Region
91, 92, 93, 94. Data group
200. Contrast image

The invention claimed is:

1. An ultrasonic diagnostic device comprising:
one or more processors configured to:
  select, from among a plurality of contrast images acquired from a cross-section containing a target of a subject to which a contrast agent has been administered, a first contrast image representing a state in which the target is stained in a first time phase, a second contrast image for determining whether the contrast agent has been discharged from the target in a second time phase after the first time phase, and a third contrast image for determining whether the contrast agent has been discharged from the target in a third time phase after the second time phase;
  identify a first major/minor relationship between a characteristic value of the target and the characteristic value of tissue being compared to the target in the first contrast image, a second major/minor relationship between the characteristic value of the target and the characteristic value of the tissue in the second contrast image, and a third major/minor relationship between the characteristic value of the target and the characteristic value of the tissue in the third contrast image;
  determine whether all of the first major/minor relationship, the second major/minor relationship, and the third major/minor relationship indicate that the characteristic value of the target is greater than the characteristic value of the tissue, or that the characteristic value of the target is less than the characteristic value of the tissue;
  generate an image to determine whether the contrast agent has been discharged from the target in the second and third time phases using data from the target and data from the tissue, based on determining that all of the first major/minor relationship, the second major/minor relationship, and the third major/minor relationship do not indicate that the characteristic value of the target is greater than the characteristic value of the tissue, or that the characteristic value of the target is less than the characteristic value of the tissue; and
  generate the image to determine whether the contrast agent has been discharged from the target in the second and third time phases using only the data from the target, based on determining that all of the first major/minor relationship, the second major/minor relationship, and the third major/minor relationship indicate that the characteristic value of the target is greater than the characteristic value of the tissue, or that the characteristic value of the target is less than the characteristic value of the tissue.

2. The ultrasonic diagnostic device according to claim 1, wherein the first major/minor relationship represents a first difference value between the characteristic value of a region of interest of the target and the characteristic value of a region of interest of the tissue in the first contrast image;
  the second major/minor relationship represents a second difference value between the characteristic value of the region of interest of the target and the characteristic value of the region of interest of the tissue in the second contrast image; and
  the third major/minor relationship represents a third difference value between the characteristic value of the region of interest of the target and the characteristic value of the region of interest of the tissue in the third contrast image.

3. The ultrasonic diagnostic device according to claim 1, wherein when the user interface accepts a user command to assign a region of interest to the a contrast image from among the plurality of contrast images, the one or more processors assign the region of interest to the contrast image, and the region of interest is located at a point where the user wants to confirm timing when the contrast agent is discharged.

4. The ultrasonic diagnostic device according to claim 3, wherein the one or more processors are further configured to:
  select a first pixel from the region of interest assigned to the contrast image;
  read the characteristic value of the tissue of the second contrast image at the second time phase;
  read the luminance value of a second pixel corresponding to the first pixel in the contrast image from the second contrast image at the second time phase;
  calculate a fourth difference value between the characteristic value of the tissue and the luminance value of the second pixel in the second contrast image at the second time phase;
  read the characteristic value of the tissue of the third contrast image at the third time phase;
  read the luminance value of a third pixel corresponding to the first pixel in the contrast image from the third contrast image at the third time phase;
  calculate a fifth difference value between the characteristic value of the tissue and the luminance value of the third pixel in the third contrast image at the third time phase; and
  assign a color in the first pixel of the contrast image based on the combination of the fourth difference value and the fifth difference value.

5. The ultrasonic diagnostic device according to claim 4, wherein a color map is stored in memory; and the one or more processors perform:

specifying a color corresponding to the combination of the fourth difference value and the fifth difference value from the color map, and assigning the specified color as the color in the first pixel.

6. The ultrasonic diagnostic device according to claim 3, wherein the one or more processors are further configured to:

select a first pixel from the region of interest of the contrast image;

read a luminance value of a second pixel corresponding to the first pixel in the contrast image from the first contrast image at the first time phase;

read the luminance value of a third pixel corresponding to the first pixel in the contrast image from the second contrast image at the second time phase;

read the luminance value of a fourth pixel corresponding to the first pixel in the contrast image from the third contrast image at the third time phase;

calculate the fourth difference value between the luminance value of the second pixel and the luminance value of the third pixel;

calculate the fifth difference value between the luminance value of the second pixel and the luminance value of the fourth pixel; and assign a color in the first pixel of the contrast image based on the combination of the fourth difference value and the fifth difference value.

7. The ultrasonic diagnostic device according to claim 6, wherein a color map is stored in memory; and the one or more processors perform:

specifying a color corresponding to the combination of the fourth difference value and the fifth difference value from the color map, and assigning the specified color as the color in the first pixel.

8. The ultrasonic diagnostic device according to claim 4, wherein the second time phase is the early phase and the third time phase is the late phase.

9. The ultrasonic diagnostic device according to claim 2, wherein the characteristic value is the average luminance within the region of interest.

10. The ultrasonic diagnostic device according to claim 1, wherein the target is a tumor and the tissue is liver parenchyma.

11. A non-transitory computer readable storage medium storing one or more instructions executable by one or more processors that, when executed by the one or more processors, cause the one or more processors to:

select, from among a plurality of contrast images acquired from a cross-section containing a target of a subject to which a contrast agent has been administered, a first contrast image representing a state in which the target is stained in a first time phase, a second contrast image for determining whether the contrast agent has been discharged from the target in a second time phase after the first time phase, and a third contrast image for determining whether the contrast agent has been discharged from the target in a third time phase after the second time phase;

identify a first major/minor relationship between a characteristic value of the target and the characteristic value of tissue being compared to the target in the first contrast image, a second major/minor relationship between the characteristic value of the target and the characteristic value of the tissue in the second contrast image, and a third major/minor relationship between the characteristic value of the target and the characteristic value of the tissue in the third contrast image;

determine whether all of the first major/minor relationship, the second major/minor relationship, and the third major/minor relationship indicate that the characteristic value of the target is greater than the characteristic value of the tissue, or that the characteristic value of the target is less than the characteristic value of the tissue;

generate an image to determine whether the contrast agent has been discharged from the target in the second and third time phases using data from the target and data from the tissue, based on determining that all of the first major/minor relationship, the second major/minor relationship, and the third major/minor relationship do not indicate that the characteristic value of the target is greater than the characteristic value of the tissue, or that the characteristic value of the target is less than the characteristic value of the tissue; and generate the image to determine whether the contrast agent has been discharged from the target in the second and third time phases using only the data from the target, based on determining that all of the first major/minor relationship, the second major/minor relationship, and the third major/minor relationship indicate that the characteristic value of the target is greater than the characteristic value of the tissue, or that the characteristic value of the target is less than the characteristic value of the tissue.

12. A method comprising:

selecting, from among a plurality of contrast images acquired from a cross-section containing a target of a subject to which a contrast agent has been administered, a first contrast image representing a state in which the target is stained in a first time phase, a second contrast image for determining whether the contrast agent has been discharged from the target in a second time phase after the first time phase, and a third contrast image for determining whether the contrast agent has been discharged from the target in a third time phase after the second time phase;

identifying a first major/minor relationship between a characteristic value of the target and the characteristic value of tissue being compared to the target in the first contrast image, a second major/minor relationship between the characteristic value of the target and the characteristic value of the tissue in the second contrast image, and a third major/minor relationship between the characteristic value of the target and the characteristic value of the tissue in the third contrast image;

determining whether all of the first major/minor relationship, the second major/minor relationship, and the third major/minor relationship indicate that the characteristic value of the target is greater than the characteristic value of the tissue, or that the characteristic value of the target is less than the characteristic value of the tissue; and generating an image to determine whether the contrast agent has been discharged from the target in the second and third time phases using only data from the target, based on determining that all of the first major/minor relationship, the second major/minor relationship, and the third major/minor relationship indicate that the characteristic value of the target is greater than the characteristic value of the tissue, or that the characteristic value of the target is less than the characteristic value of the tissue.

\* \* \* \* \*